United States Patent [19]

Duggan et al.

[11] Patent Number: 4,897,402
[45] Date of Patent: Jan. 30, 1990

[54] 5-OXA, 5-THIA, 5-AZA HMG-COA REDUCTASE INHIBITORS

[75] Inventors: Mark E. Duggan, Wynnewood; George D. Hartman, Lansdale, both of Pa.

[73] Assignee: Merck & Co., Inc., Rahway, N.J.

[21] Appl. No.: 212,767

[22] Filed: Jun. 29, 1988

[51] Int. Cl.$^4$ .............................. A61K 31/19
[52] U.S. Cl. ..................... 514/312; 514/82; 514/96; 514/99; 514/100; 514/432; 514/456; 514/824; 549/5; 549/23; 549/220; 549/292; 549/399; 549/400; 548/413; 548/518; 548/525; 548/527; 546/22; 546/23; 546/153; 546/155; 546/196; 546/200; 546/202
[58] Field of Search ............... 549/292, 399, 400, 23; 546/153, 155; 514/456, 432, 312

Primary Examiner—Richard L. Raymond
Assistant Examiner—Amelia A. Owens
Attorney, Agent, or Firm—Melvin Winokur; Joseph F. DiPrima

[57] ABSTRACT

Novel HMG-CoA reductase inhibitors are useful as antihypercholesterolemic agents and are represented by stuctural formulae (I) and (II):

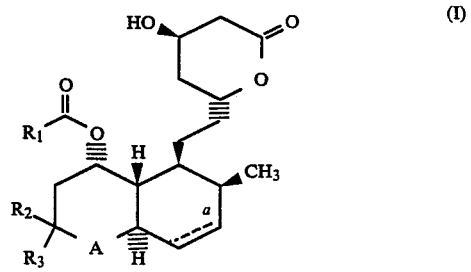

(I)

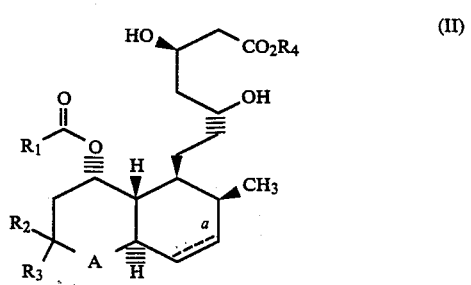

(II)

wherein A is O, S(O)$_n$ or N—R$_{13}$.

18 Claims, No Drawings

5-OXA, 5-THIA, 5-AZA HMG-COA REDUCTASE INHIBITORS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR® (lovastatin), now commercially available, is one of a group of very active antihypercholesterolemic agents that functions by limiting cholesterol biosynthesis by inhibiting the enzyme HMG-CoA reductase. In addition to the natural fermentation products, mevastatin and lovastatin, there are a variety of semi-synthetic and totally synthetic analogs thereof.

The naturally occurring compounds and their semi-synthetic analogs have the following general structural formulae:

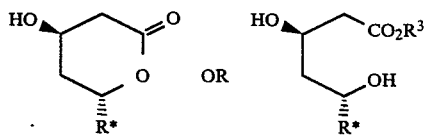

wherein:
$R^3$ is hydrogen, $C_{1-5}$ alkyl or $C_{1-5}$ alkyl substituted with a member of the group consisting of phenyl, dimethylamino, or acetylamino; and
+ is
+ is

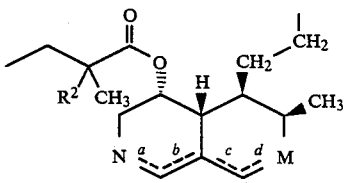

wherein
N is

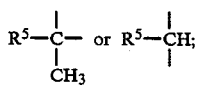

$R^5$ is H or OH; M is

$R^6$ is hydrogen or hydroxy; $R^2$ is hydrogen or methyl; and a, b, c, and d represent single bonds, one of a, b, c or d represents a double bond, or both a and c or both b and d represent double bonds provided that when a is a double bond,
N is

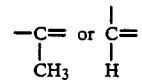

and when d is a double bond, M is

U.S. patent application Ser. No. 048,136 filed May 15, 1987 discloses 6-substituted compounds of the above general formula wherein $R^-$ is

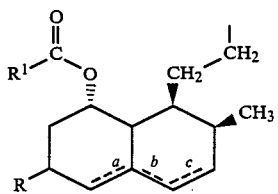

wherein R is

$CH_2OH$, $CH_2OCR^4$, $CO_2R^7$ or $CNR^8R^9$;

and $R^1$, $R^4$, $R^7$, $R^8$ and $R^9$ are broadly defined organic moieties.

U.S. patent application Ser. No. 142,361 filed Jan. 7, 1988 discloses lovastatin analogs wherein the 6-position is gem-disubstituted:

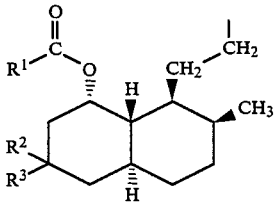

$R^2$ and $R^3$ are alkyl or substituted alkyl moieties.

DETAILED DESCRIPTION OF THE INVENTION

This invention relates to novel compounds which are useful as HMG-CoA reductase inhibitors. The specific HMG-CoA reductase inhibitors of this invention are the compounds represented by structural formulae (I) and (II):

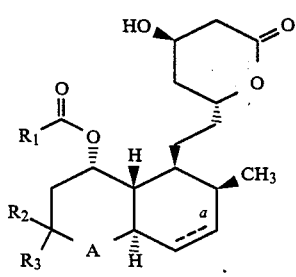

(I)

-continued

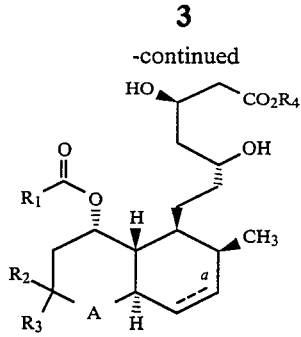
(II)

wherein:

A is O or

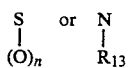

n is 0 to 2;

$R_1$ is selected from:
(1) $C_{1-10}$ alkyl;
(2) substituted $C_{1-10}$ alkyl in which one or more substituent(s) is selected from
 (a) halogen,
 (b) hydroxy,
 (c) $C_{1-10}$ alkoxy,
 (d) $C_{1-5}$ alkoxycarbonyl,
 (e) $C_{1-5}$ acyloxy,
 (f) $C_{3-8}$ cycloalkyl,
 (f) $C_{3-8}$ cycloalkyl,
 (g) phenyl,
 (h) substituted phenyl in which the substituents are X and Y,
 (i) $C_{1-10}$ alkylS(O)$_n$ in which n is 0 to 2,
 (j) $C_{3-8}$ cycloalkylS(O)$_n$,
 (k) phenylS(O)$_n$.
 (l) substituted phenylS(O)$_n$ in which the substituents are X and Y, and
 (m) oxo;
(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is selected from
 (a) $C_{1-10}$ alkyl
 (b) substituted $C_{1-10}$ alkyl in which the substituent is selected from
  (i) halogen,
  (ii) hydroxy,
  (iii) $C_{1-10}$ alkoxy,
  (iv) $C_{1-5}$ alkoxycarbonyl,
  (v) $C_{1-5}$ acyloxy,
  (vi) phenyl,
  (vii) substituted phenyl in which the substituents are X and Y
  (viii) $C_{1-10}$ alkylS(O)n,
  (ix) $C_{3-8}$ cycloalkylS(O)n,
  (x) phenylS(O)n,
  (xi) substituted phenylS(O)n in which the substituents are X and Y, and
  (xii) oxo,
 (c) $C_{1-10}$ alkylS(O)n,
 (d) $C_{3-8}$ cycloalkylS(O)n,
 (e) phenylS(O)n,
 (f) substituted phenylS(O)n in which the substituents are X and Y,
 (g) halogen,
 (h) hydroxy,
 (i) $C_{1-10}$ alkoxy,
 (j) $C_{1-5}$ alkoxycarbonyl,
 (k) $C_{1-5}$ acyloxy,
 (l) phenyl, and
 (m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) a member selected from
 (a) piperidinyl,
 (b) pyrrolidinyl,
 (c) piperazinyl,
 (d) morpholinyl, and
 (e) thiomorpholinyl; and
(17) $R^5S$ in which $R^5$ is selected from
 (a) $C_{1-10}$ alkyl,
 (b) phenyl, and
 (c) substituted phenyl in which the substituents are X and Y;

$R^2$ and $R^3$ are independently selected from:
(1) hydrogen;
(2) $C_{1-10}$ alkyl; and
(3) substituted $C_{1-10}$ alkyl in which one or more substituents is selected from
 (a) halogen,
 (b) hydroxy,
 (c) $C_{1-10}$ alkoxy,
 (d) $C_{1-5}$ alkoxycarbonyl,
 (e) $C_{1-5}$ alkylacyloxy,
 (f) phenylacyloxy,
 (g) phenoxycarbonyl,
 (h) phenyl $C_{1-5}$ alkylacyloxy,
 (i) phenyl $C_{1-5}$ alkoxy,
 (j) amino,
 (k) $C_{1-5}$ alkylamino,
 (l) di($C_{1-5}$ alkyl)amino,
 (m) phenylamino,
 (n) substituted phenylamino in which the substituents are X and Y;
 (o) phenyl $C_{1-5}$ alkylamino,
 (p) substituted phenyl $C_{1-5}$ alkylamino in which the substituents are X and Y,
 (q) $C_{3-8}$ cycloalkyl,
 (r) phenyl,
 (s) substituted phenyl in which the substituents are X and Y,
 (t) phenylS(O)n,
 (u) substituted phenyl S(O)n in which the substituents are X and Y,
 (v) phenyl $C_{1-5}$ alkyl S(O)n,
 (w) $C_{1-5}$ alkylS(O)n,
 (x) phenylaminoacyloxy,
 (y) $C_{1-5}$ alkylaminoacyloxy,
 (z) $C_{1-5}$ alkylacylamino,
 (aa) di(phenyl$C_{1-5}$alkyl)phosphonyl,
 (bb) di($C_{1-5}$alkyl)phosphinyl, (cc) phenyl$C_{1-5}$ alkylacylamino;
(4) $R_2$ and $R_3$ together with the carbon atom to which they are attached form a $C_{3-8}$ carbocyclic ring;

$R_4$ is selected from:
(1) hydrogen;
(2) $C_{1-5}$ alkyl;
(3) substituted $C_{1-5}$ alkyl in which the substituent is selected from
 (a) phenyl,
 (b) dimethylamino, and
 (c) acetylamino, and
(4) 2,3 dihydroxypropyl;

$R_{13}$ is selected from:
(1) hydrogen;
(2) $C_{1-5}$ alkyl;
(3) substituted $C_{1-5}$ alkyl in which the substituent is selected from:
 (a) phenyl,
 (b) dimethylamino, and
 (c) acetylamino, and
 (d) hydroxy, provided that hydroxy is substituted only at C-2, C-3, C-4 or C-5; and
 (e) $C_{1-5}$ alkoxy;
(4) $C_{1-5}$ alkylcarbonyl;
(5) $C_{1-5}$ alkyloxycarbonyl;
(6) $C_{1-5}$ alkylaminocarbonyl;

X and Y independently are hydrogen, halogen, trifluoromethyl, $C_{1-3}$ alkyl, nitro, cyano or a group selected from:
(1) $R_6O\ (CH_2)_m$ in which m is 0 to 3 and $R_6$ is hydrogen, $C_{1-3}$ alkyl or hydroxy-$C_{2-3}$ alkyl;
(2)

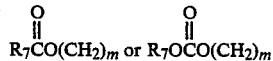

in which $R_7$ is hydrogen, $C_{1-3}$ alkyl,
hydroxy-$C_{2-3}$ alkyl, phenyl, naphthyl,
amino-$C_{1-3}$ alkyl, $C_{1-3}$ alkylamino
$C_{1-3}$ alkyl, di($C_{1-3}$ alkyl)amino-$C_{1-3}$ alkyl, hydroxy-$C_{2-3}$ alkylamino-$C_{1-3}$ alkyl, or di(hydroxy-$C_{2-3}$ alkyl)amino-$C_{1-3}$ alkyl; provided that in

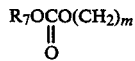

$R_7$ is not H;
(3)

in which $R_8$ is hydrogen, $C_{1-3}$alkyl, hydroxy-$C_{2-3}$-alkyl, $C_{1-3}$alkoxy $C_{1-3}$ alkyl, phenyl or naphthyl;
(4) $R_9R_{10}N(CH_2)_m, R_9R_{10}NC(CH_2)_m$

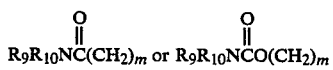

in which $R_9$ and $R_{10}$ independently are hydrogen, $C_{1-3}$ alkyl, hydroxy $C_{2-3}$ alkyl or $R_9$ and $R_{10}$ together with the nitrogen atom to which they are attached form a heterocyclic group selected from piperidinyl, pyrrolidinyl, piperazinyl, morpholinyl or thiomorpholinyl;
(5) $R_{11}S(O)n(CH_2)_m$ in which $R_{11}$ is hydrogen, $C_{1-3}$ alkyl, amino, $C_{1}$-alkylamino or di($C_{1}$-alkyl)amino; is a single bond or a double bond; halogen is F or Cl;

or a pharmaceutically acceptable salt thereof.

Except where specifically defined to the contrary, the terms "alkyl", "alkoxy" and "acyl" include both the straight-chain and branched-chain species of the term.

One embodiment of this invention is the class of compounds of the formulae (I) and (II) wherein:

A is O or S(O)n;
$R_1$ is selected from:
(1) $C_{1-10}$ alkyl;
(2) substituted $C_{1-10}$ alkyl in which one or more substituent(s) is selected from
 (a) halogen,
 (b) hydroxy,
 (c) $C_{1-10}$ alkoxy,
 (d) $C_{1-5}$ alkoxycarbonyl,
 (e) $C_{1-5}$ acyloxy,
 (f) $C_{3-8}$ cycloalkyl,
 (g) phenyl,
 (h) substituted phenyl in which the substituents are X and Y, and
 (i) oxo;
(3) $C_{3-8}$ cycloalkyl;
(4) substituted $C_{3-8}$ cycloalkyl in which one substituent is selected from
 (a) $C_{1-10}$ alkyl,
 (b) substituted $C_{1-10}$ alkyl in which the substituent is selected from
  (i) halogen,
  (ii) hydroxy,
  (iii) $C_{1-10}$ alkoxy,
  (iv) $C_{1-5}$ acyloxy,
  (v) $C_{1-5}$ alkoxycarbonyl,
  (vi) phenyl,
  (vii) substituted phenyl in which the substituents are X and Y, and
  (viii) oxo,
 (c) halogen,
 (d) hydroxy,
 (e) $C_{1-10}$ alkoxy,
 (f) $C_{1-5}$ alkoxycarbonyl,
 (g) $C_{1-5}$ acyloxy,
 (h) phenyl,
 (i) substituted phenyl in which the substituents are X and Y;
(5) phenylamino;
(6) substituted phenylamino in which the substituents are X and Y;
(7) phenyl$C_{1-10}$alkylamino; and
(8) substituted phenyl $C_{1-10}$ alkylamino in which the substituents are X and Y;

$R^2$ and $R^3$ are independently selected from
(1) hydrogen;
(2) $C_{1-10}$ alkyl;
(3) substituted $C_{1-10}$ alkyl in which one or more substituents is selected from:
 (a) halogen,
 (b) hydroxy, or
 (c) amino;
(4) $CH_2R^{12}$ in which $R^{12}$ is selected from:
 (a) $C_{1-5}$ alkoxy,
 (b) $C_{1-5}$ alkoxycarbonyl,
 (c) $C_{1-5}$ alkylacyloxy,
 (d) phenylacyloxy,
 (e) phenoxycarbonyl,
 (f) phenyl$C_{1-5}$alkylacyloxy, (g) phenylC$_{1-5}$ alkoxy
(h) C$_{1-5}$ alkylamino,
(i) di(C$_{1-5}$ alkyl)amino,
(j) phenylamino,
(k) substituted phenylamino in which the substituents are X and Y,
(l) phenyl C$_{1-5}$alkylamino,
(m) substituted phenyl C$_{1-5}$ alkyl amino in which the substituents are X and Y,
(n) C$_{3-8}$ cycloalkyl,
(o) phenyl,
(p) substituted phenyl in which the substituents are X and Y,
(q) phenylS(O)$_n$,
(r) substituted phenylS(O)$_n$ in which the substituents are X and Y,
(s) phenyl C$_{1-5}$ alkylS(O)$_n$,
(t) C$_{1-5}$ alkylS(O)n,
(u) phenylaminoacyloxy,
(v) C$_{1-5}$ alkylaminoacyloxy,
(w) C$_{1-5}$ alkylacylamino,
(x) di(phenylC$_{1-5}$alkyl)phosphonyl,
(y) di(C$_{1-5}$alkyl)phosphinyl,
(z) phenylC$_{1-5}$ alkylacylamino;

(5) R$^2$ and R$^3$ together with the carbon atom to which they are attached form a C$_{3-8}$ carbocyclic ring.

One subclass of this embodiment is the compounds of the formulae (I) and (II) wherein:
R$_1$ is selected from:
(1) C$_{1-10}$ alkyl;
(2) C$_{3-8}$ cycloalkyl;
(3) phenylamino; and
(4) substituted phenylamino in which the substituents are X and Y.

Illustrative of this subclass are those compounds of the formulae (I) and (II) wherein
R$_2$ and R$_3$ are independently selected from:
(1) hydrogen;
(2) C$_{1-5}$alkyl;
(3) C$_{1-5}$ alkyl substituted with hydroxy;
(4) CH$_2$R$^{12}$ in which R$^{12}$ is selected from:
(a) C$_{1-5}$alkoxy,
(b) C$_{1-5}$ alkoxycarbonyl,
(c) C$_{1-5}$ alkylacyloxy,
(d) phenylacyloxy,
(e) phenoxycarbonyl,
(f) phenylC$_{1-5}$alkylacyloxy,
(g) phenylC$_{1-5}$alkoxy,
(h) phenyl S(O)$_n$,
(i) substituted phenyl S(O)$_n$ in which the substituents are X and Y,
(j) phenylC$_{1-5}$ alkyl S(O)$_n$,
(k) C$_{1-5}$alkyl S(O)$_n$,
(l) phenylaminoacyloxy,
(m) C$_{1-5}$alkylaminoacyloxy,
(n) phenyl,
(o) substituted phenyl in which the substituents are X and Y;
(p) C$_{1-5}$alkylacylamino;
(q) phenylC$_{1-5}$alkylacylamino;
(r) di(phenylC$_{1-5}$alkyl)phosphon-yl;
(s) di(C$_{1-5}$alkyl)phosphinyl Further illustrating this subclass are those compounds of formulae (I) and (II) wherein:
A is O; a is a single bond; and
R$_1$ is 2-methyl-2-butyl or 2-butyl; and R$_2$ and R$_3$ are independently selected from: H, CH$_3$, phenylthiomethyl and hydroxymethyl.

Exemplifying this illustration are the following compounds of the formulae (I) and (II):
(1) 6(R)-[2-[8(S)-(2,2-dimethylbutyryloxy)-2(S)-methyl-5 -oxa-6,6-dimethyl-1,2,3,4,4a(R),7,8,-8a(R)-octahydronaphthyl 1(S)]ethyl]4(R) hydroxy 3,4,5,6-tetrahydro-2H-pyran-2-one. (hereafter referred to as compound 9)
(2) 6(R)-[2-[8(S)-methyl-5-oxa-6-(S)-(phenylthiomethyl, methyl) 1,2,3,4,4a(R),7,8,8a(R) octahydronaphthyl-1(S)]-ethyl]-4(R) hydroxy 3,4,5,6-tetrahydro-2H-pyran 2-one. (hereafter referred to as compound 10)
(3) 6(R)-[2-[8(S)-(2,2 dimethylbutyryloxy)-2(S)-methyl-5 -oxa-6(R)-(phenylthiomethyl, methyl)-1,2,3,4,4a(R),7,8,8a(R)-octahydronaphthyl-1(S)]ethyl]4(R) hydroxy-3,4,5,6-tetrahydro-2H-pyran-2-one. (hereafter referred to as compound 11)
(4) 6(R)-[2 [8(S)-(2-methylbutyryloxy)-2(S)-methyl-5-oxa-6,6-dimethyl-1,2,3,4,4a(R),7,8,8a(R)-octahydronaphthyl-1(S)]ethyl]4(R)-hydroxy-3,4,5,6-tetrahydro-2H-pyran-2-one.
(5) 6(R)-[2-[8(S)-(2,2 -dimethylbutyryloxy)-2(S)-methyl-5-oxa-6(S)-(hydroxymethyl, methyl)-1,2,3,4,4a(R),7,8,8a(R)-octahydronaphthyl-1(S)]ethyl]4(R)-hydroxy-3,4,5,6-tetrahydro-2H-pyran-2-one.
(6)-6(R)-[2 [8(S)-(2,2-dimethylbutyryloxy) 2(S)- methyl-5 oxa-6(R) (hydroxymethyl, methyl) 1,2,3, 4,4a(R),7,8,8a(R)-octahydronaphthyl-1(S)]ethyl]4(R)-hydroxy-3,4,5,6-tetrahydro-2H-pyran-2-one.
(7) 6(R)-[8(S)-(2,2-dimethylbutyryloxy)-2(S)-methyl-5-oxa-6(S)-(phenylthiomethyl, hydroxymethyl)-1,2,3,4,41(R),7,8,8a(R)-octahydro-naphthyl-1(S)]ethyl]-4(R)-hydroxy-3,4,5,6-tetrahydro-2H pyran 2-one.
(8) 6(R) [2-[8(S) (2,2 dimethylbutyryloxy) 2(S) methyl 5-oxa 6(R) (phenylthiomethyl, hydroxy methyl)-1,2,3,4,4a(R),7,8,8a(R)-octahydronaphthyl 1(S)]ethyl]-4(R) hydroxy 3,4,5,6 tetrahydro-2H-pyran-2-one.

A second illustration of this subclass are those compounds of formulae (I) and (II) wherein:
A is S(O)$_n$; a is a single bond;
R$_1$ is 2-methyl-2-butyl or 2-butyl; and
R$_2$ and R$_3$ are independently selected from:
H, CH$_3$ and hydroxymethyl.

Exemplifying this second illustration are the following compounds of formulae (I) and (II):
(1) 6(R)-[2 [8(S)-(2,2-dimethylbutyryloxy)-2(S)-methyl-5-thia-6,6-dimethyl 1,2,3,4,4a(R),7,8,8a(R)-octahydronaphthyl-1(S)]ethyl]-4(R) hydroxy3,4,5,6-tetrahydro-2H-pyran-2-one.
(2) 6(R) [2-[8(S) (2,2-dimethylbutyryloxy)-2(S)-methyl-5 thia 6(S) (hydroxymethyl, methyl) 1,2,3,4,4a,7,8,,8a(R) octahydronaphthyl-1(S)]ethyl]4(R) hydroxy 3,4,5,6-tetrahydro-2H-pyran-2-one.
(3) 6(R) [2-[8(S)-(2,2-dimethylbutyryloxy)-2-(S)-methyl-5-thia 6(R)-(hydroxymethyl, methyl)-1,2,3,4,4a,7,8,8a(R)-octahydronaphthyl-1(S)]ethyl]-4(R)-hydroxy-3,4,5,6-tetrahydro-2H-pyran-2-one.
(4) 6(R) [2-[8(S)-(2,2 dimethylbutyryloxy) 2(S) methyl thia 6(S)-(hydroxymethyl) 1,2,3,4,4a,6,7,8,8a(R)-nonahydronaphthyl-1(S)]ethyl]4(R) hydroxy3,4,5,6-tetrahydro-2H-pyran-2-one.
(5) 6(R) [2 [8(S) (2,2 dimethylbutyryloxy) 2(S) methyl thia 6(R) (hydroxymethyl) 1,2,3,4,4a,6,7,8,8a(R)

nonahydronaphthyl 1(S)]ethyl]4(R) hydroxy 3,4,5,6-tetrahydro-2H-pyran 2 one.

(6) 6(R) [2 [8(S) (2,2 dimethylbutyryloxy)-2(S)-methylthia-5,5 dioxide 6,6 dimethyl 1,2,3,4,4a(R),7,8,- a(R)-octahydronaphthyl-1(S)]ethyl]4(R) hydroxy-3,4,5,6-tetrahydro-2H-pyran-2-one.

In a second embodiment is the compounds of formula (I) and (II) wherein
A is N-R$^{13}$;
R$_1$ is selected from:
  (1) C$_{1-10}$ alkyl;
  (2) substituted C$_{1-10}$ alkyl in which one or more substituent(s) is selected from
    (a) halogen,
    (b) hydroxy,
    (c) C$_{1-10}$ alkoxy,
    (d) C$_{1-5}$ alkoxycarbonyl,
    (e) C$_{1-5}$ acyloxy,
    (f) C$_{3-8}$ cycloalkyl,
    (g) phenyl,
    (h) substituted phenyl in which the substituents are X and Y, and
    (i) oxo;
  (3) C$_{3-8}$ cycloalkyl;
  (4) substituted C$_{3-8}$ cycloalkyl in which one substituent is selected from
    (a) C$_{1-10}$ alkyl,
    (b) substituted C$_{1-10}$ alkyl in which the substituent is selected from
      (i) halogen,
      (ii) hydroxy,
      (iii) C$_{1-10}$ alkoxy
      (iv) C$_{1-5}$ acyloxy,
      (v) C$_{1-5}$ alkoxycarbonyl,
      (vi) phenyl,
      (vii) substituted phenyl in which the substituents are X and Y, and
      (viii) oxo,
    (c) halogen,
    (d) hydroxy,
    (e) C$_{1-10}$ alkoxy,
    (f) C$_{1-5}$ alkoxycarbonyl,
    (g) C$_{1-5}$ acyloxy,
    (h) phenyl,
    (i) substituted phenyl in which the substituents are X and Y;
  (5) phenylamino;
  (6) substituted phenylamino in which the substituents are X and Y;
  (7) phenylC$_{1-10}$alkylamino; and
  (8) substituted phenyl C$_{1-10}$ alkylamino in which the substituents are X and Y;
R$^2$ and R$^3$ are independently selected from
  (1) hydrogen;
  (2) C$_{1-10}$ alkyl;
  (3) substituted C$_{1-10}$ alkyl in which one or more substituents is selected from:
    (a) halogen,
    (b) hydroxy,
    (c) amino;
  (4) CH$_2$R$^{12}$ in which R$^{12}$ is selected from:
    (a) C$_{1-5}$ alkoxy,
    (b) C$_{1-5}$ alkoxycarbonyl,
    (c) Cl5 alkylacyloxy,
    (d) phenylacyloxy,
    (e) phenoxycarbonyl,
    (f) phenylC$_{1-5}$alkoxy,
    (h) C$_{1-5}$ alkylamino,
    (i) di(C$_{1-5}$alkyl)amino,
    (j) phenylamino,
    (k) substituted phenylamino in which the substituents are X and Y,
    (l) phenyl C$_{1-5}$ alkylamino,
    (m) substituted phenyl C$_{1-5}$ alkyl amino in which the substituents are X and Y,
    (n) C$_{3-8}$ cycloalkyl,
    (o) phenyl,
    (p) substituted phenyl in which the substituents are X and Y,
    (q) phenylS(O)$_n$,
    (r) substituted phenylS(O)$_n$ in which the substituents are X and Y,
    (s) phenyl C$_{1-5}$ alkylS(O)$_n$,
    (t) C$_{1-5}$ alkylS(O)$_n$,
    (u) phenylaminoacyloxy,
    (v) C$_{1-5}$ alkylaminoacyloxy,
    (w) C$_{1-5}$ alkylacylamino,
    (x) di(phenylCl 5alkyl)phosphonyl,
    (y) di(C$_{1-5}$alkyl)phospinyl;
  (5) R$^2$ and R$^3$ together with the carbon atom to which they are attached form a C$_{3-8}$ carbocyclic ring.

One subclass of this embodiment is the compounds of the formulae (I) and (II) wherein:
R$_1$ is selected from:
  (1) C$_{1-10}$ alkyl;
  (2) C$_{3-8}$ cycloalkyl;
  (3) phenylamino; and
  (4) substituted phenylamino in which the substituents are X and Y.
R$_{13}$ is selected from:
  (1) hydrogen;
  (2) C$_{1-5}$ alkyl;
  (3) phenylC$_{1-5}$ alkyl;
  (4) C$_{1-5}$ alkylcarbonyl.

Illustrative of this subclass are those compounds of the formulae (I) and (II) wherein R$_2$ and R$_3$ are independently selected from:
  (1) hydrogen;
  (2) C$_{1-5}$alkyl;
  (3) C$_{1-5}$ alkyl substituted with hydroxy;
  (4) CH$_2$R$^{12}$ in which R$^{12}$ is selected from:
    (a) C$_{1-5}$ alkoxy,
    (b) C$_{1-5}$ alkoxycarbonyl,
    (c) C$_{1-5}$alkylacyloxy,
    (d) phenylacyloxy,
    (e) phenoxycarbonyl,
    (f) phenylC$_{1-5}$ alkylacyloxy,
    (g) phenylC$_{1-5}$alkoxy,
    (h) phenyl S(O)$_n$,
    (i) substituted phenyl S(O)$_n$ in which the substituents are X and Y,
    (j) phenylalkyl S(O)$_n$,
    (k) C$_{1-5}$ alkyl S(O)$_n$,
    (l) phenylaminoacyloxy,
    (m) C$_{1-5}$ alkylaminoacyloxy,
    (n) phenyl,
    (o) substituted phenyl in which the substituents are X and Y.

The compounds of formula (I) wherein A is O and a is a single bond are prepared following Scheme 1:

SCHEME 1

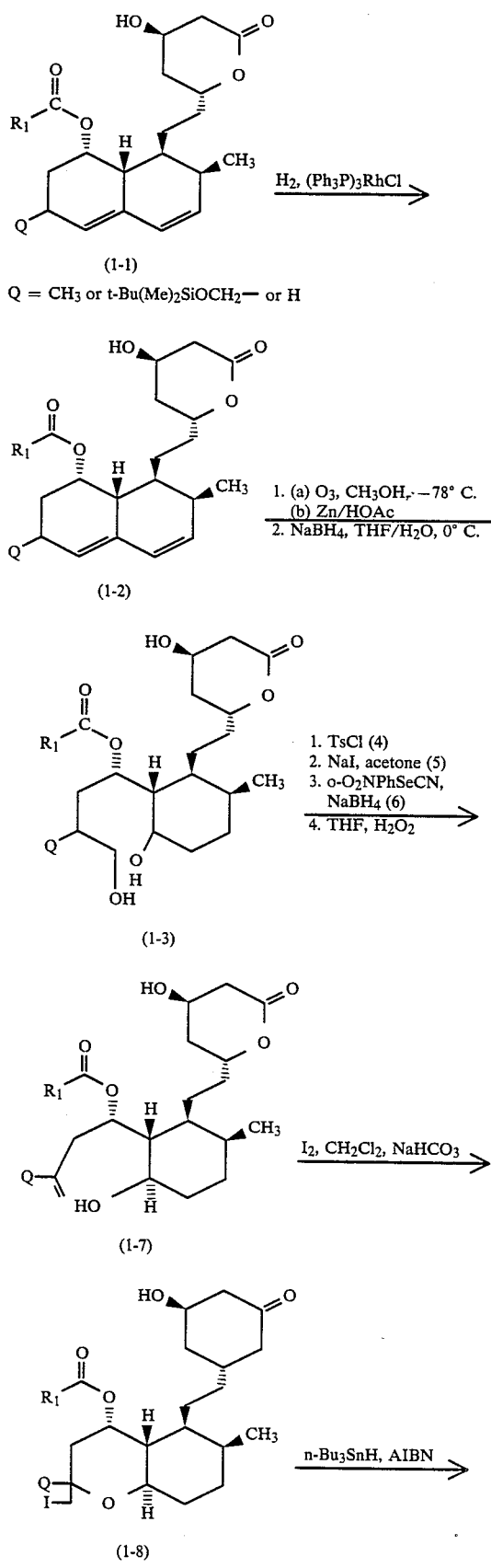

(1-1)
Q = CH₃ or t-Bu(Me)₂SiOCH₂— or H (1-2)

1. (a) O₃, CH₃OH, −78° C.
   (b) Zn/HOAc
2. NaBH₄, THF/H₂O, 0° C.

(1-3)

1. TsCl (4)
2. NaI, acetone (5)
3. o-O₂NPhSeCN, NaBH₄ (6)
4. THF, H₂O₂

(1-7)

I₂, CH₂Cl₂, NaHCO₃

(1-8)

n-Bu₃SnH, AIBN

-continued
SCHEME 1

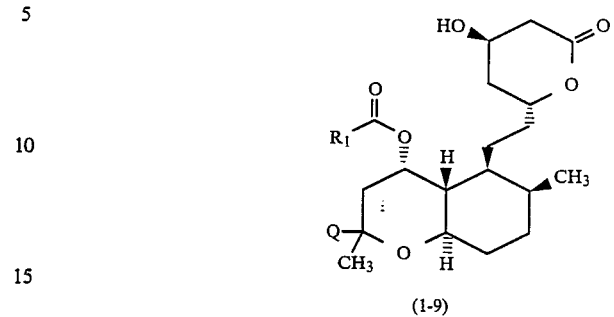

(1-9)

Compound (1-1) may be prepared from lovastatin or mevastatin by replacement, if necessary, of the 2-methylbutyryloxy moiety by $R_1CO_2$. The hydrolysis of the 8-acyloxy moiety and reesterification may be accomplished following the procedure in U.S. Pat. No. 4,444,784. The conversion to compounds (1-1) wherein Q is $CH_2OH$ and its silyl protected form can be carried out following the procedures in U.S. patent applications Ser. No. 161530, Ser. No. 161579, Ser. No. 161529 all filed on Feb. 29, 1988.

Compound (1-1) is converted to compound (1-2) by the reduction of the 3,4-double bond following the detailed procedure in U.S. patent application Ser. No. 092,804 filed Sept. 3, 1987.

The monoene (1 2) is treated with ozone in methanol at about −78° C. followed by reduction of the ozonide with Zn/acetic acid and reduction of the intermediate ketoaldehyde with NaBH₄ to yield compound (1-3) which after contact with tosyl chloride gives the tosylate (1-4). Treatment of the tosylate (1 4) with sodium iodide in acetone gives an iodide (1-5). Compound (1-7) is obtained from the iodide (1 5) by selenation with o-O₂NPhSeCN followed by oxidative elimination with THF/H₂O₂. Treatment of compound (1-7) with iodine/CH₂Cl₂ in the presence of NaHCO₃ yields compound (1-8) as a mixture of epimers. The epimeric iodides (1-8) can be reduced with a trialkyl tin hydride to afford compounds (1-9). Alternatively (Scheme 2), the epimeric iodides (1 8) can be converted to compounds of formula (2 10) by reaction with an alkyl or heteroatom moiety either by a substitution or radical coupling reaction. One example of such methodology is the cross coupling reaction between an alkyl halide and an organo metallic reagent (e.g. alkyl iodides with lithium dialkylcopper-Posner, Org. React. 22, 253-400 (1975)).

SCHEME 2

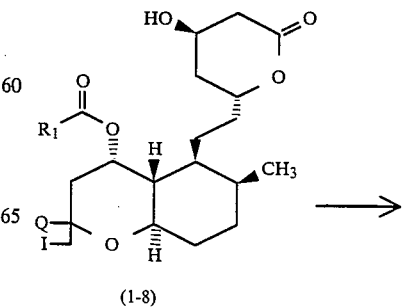

(1-8)

SCHEME 2 -continued

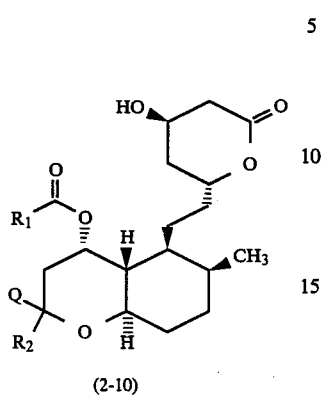

(2-10)

In the preparation of compounds (I), where $R_2$ and $R_3$ are both alkyl other than methyl or both substituted alkyl, compounds of formula (1-1) are utilized wherein Q is t-Bu(Me)$_2$SiOCH$_2$. The silyloxy protecting group of compound (2 10) is removed employing standard techniques and the resulting hydroxymethyl moiety is halogenated, e.g. triphenyl-phosphine, iodine, imidazole, followed by substitution or radical coupling with an alkyl or heteroatom moiety which results in the elaboration of CH$_2$I to $R^3$ (Scheme 2a).

SCHEME 2a

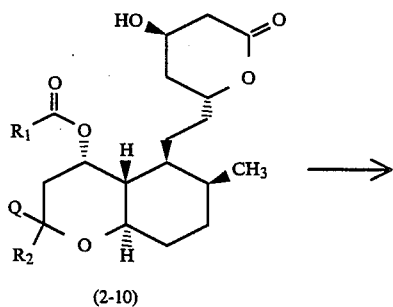

(2-10)

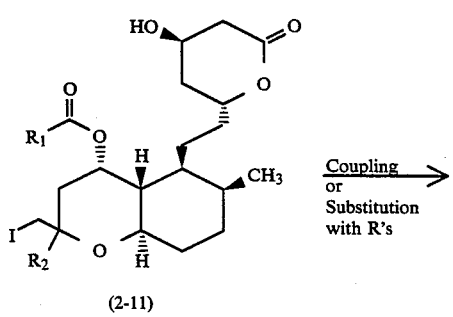

(2-11)

Coupling or Substitution with R's →

SCHEME 2a -continued

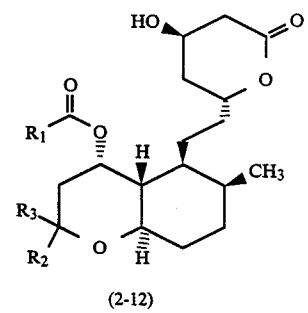

(2-12)

Compounds of formulae (I) and (II) wherein a is a double bond may be prepared following the methodology of Scheme 3. This scheme employs similar sequences to that of Scheme 1 but uses one equivalent of NaBH$_4$ to reduce the ketoaldehyde, formed from the Zn/HOAc treatment of the ozonide, to the ketone (3—3) which is followed by a Pd catalyzed dehydrogenation to insert the 3,4-double bond. The ketone (3-4) is then reduced with a second equivalent of NaBH$_4$. The primary alcohol (3-5) is iodinated (3-6), converted to the selenium derivative (3-7) and oxidized to the olefin (3-8). Treatment of compound (3-8) with iodine/CH$_2$Cl$_2$ in the presence of NaHCO$_3$ yields compounds (3 9) as a mixture of epimers. The epimeric iodides (3-9) can be reduced to compounds of formula (3-10) by reaction with a trialkyl tin hydride.

SCHEME 3

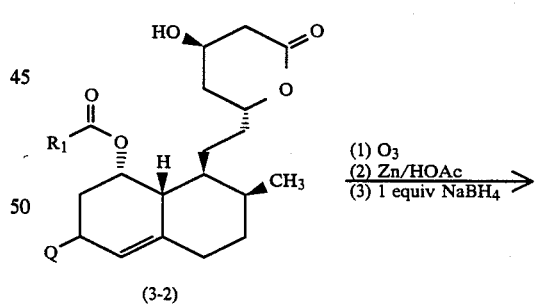

(3-2)

(1) O$_3$
(2) Zn/HOAc
(3) 1 equiv NaBH$_4$ →

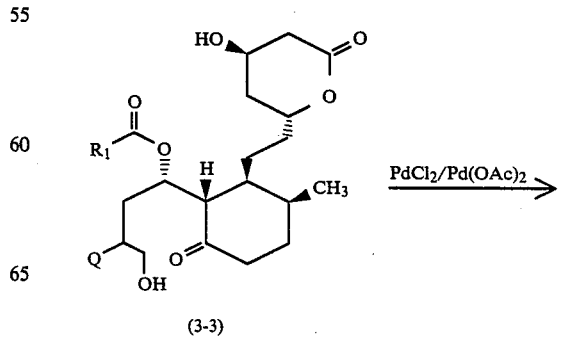

(3-3)

PdCl$_2$/Pd(OAc)$_2$ →

-continued
SCHEME 3

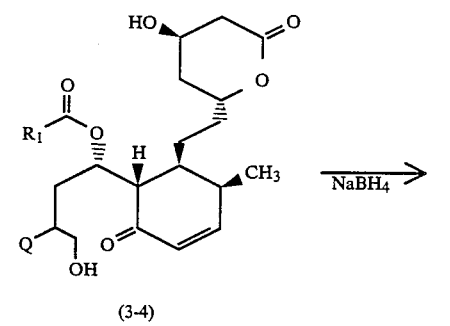

(3-4)

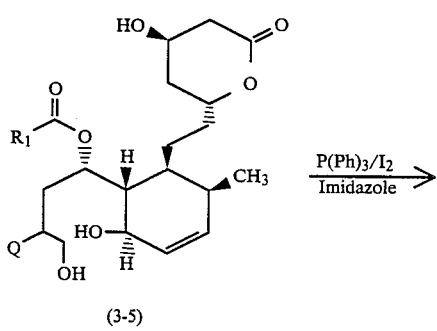

(3-5)

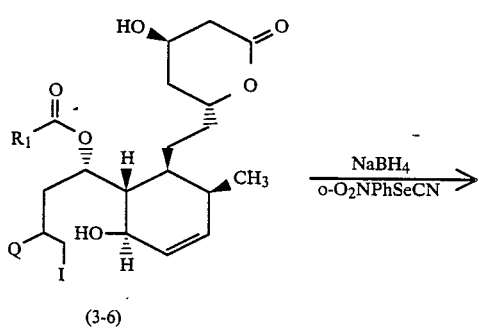

(3-6)

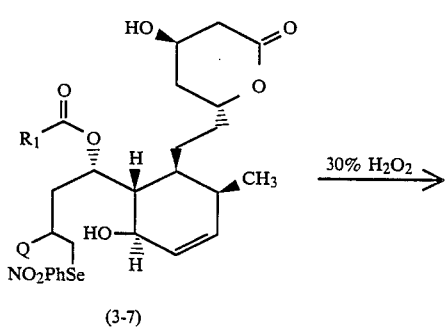

(3-7)

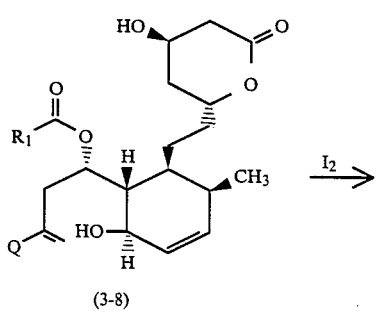

(3-8)

-continued
SCHEME 3

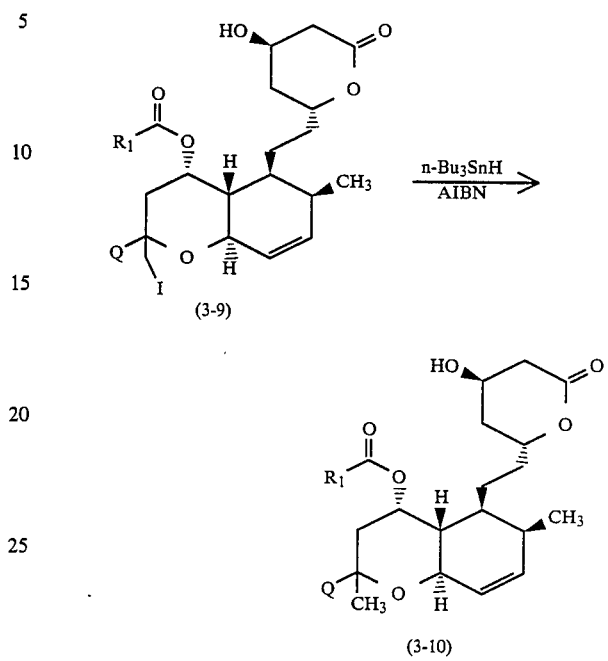

Alternatively one can start with a hexahydronaphthyl moiety as in Scheme 2 and protect the 3,4 double bond, using the method described by Kuo in U.S. Pat. No. 4,490,546, while the chemical transformations of Scheme 1 are conducted at the 4a, 5 and 6 sites. The protecting group is ultimately removed following the procedure of Kuo.

The compounds of formulae (I) and (II) wherein A is $S(O)_n$ are prepared following Schemes 4 and 4a. The lactone is reduced with diisobutyl aluminum hydride (DIBAL) followed by reaction with methanol and para-toluene sulfonic acid (PTSA) to form the acetal (4–4). Acetal (4–4) is then carried throuqh a series of reactions, analogous to those discussed in Scheme 1, to form the olefin (4–8). The 4a alcohol group of Compound (4–8) is converted to the ketone (4–9) via a Swern oxidation. If desired a double bond can be inserted into the 3,4-position of Compound (4–9) by a Pd catalyzed dehydrogenation to form Compound (4–10). The 4a-keto moiety of Compound (4–10) is converted to a thioketone (4–11) by employing 2,4 bis(4 methoxyphenyl) 1,3,2,4 dithiadi- phosphetane-2,4 disulfide and following the procedure of Pederson et al., Bull. Soc. Chem. Belg., 87 223, (1978). The thioketone (4–11) is reduced to the mercaptan (4–12) followed by cyclization to the sulfide (4–13) employing the method described by Stacey et al., Organic Reactions, Vol. 13, p. 150, John Wiley & Sons (1963). The acetal moiety is converted back to the lactone, the hydroxyl protecting group removed, and if desired the sulfide group oxidized with m chloroperbenzoic acid (m-CPBA) to form Compound (4–14) The hydroxymethyl moiety of Compound (4–14) can be elaborated to $R_2$ (Compound (4–15)) by conversion to the halomethyl group followed by substitution or coupling with an alkyl or heteroatom moiety as discussed above in Scheme 2. The identity and employment of Q is analogous to that previously discussed in Schemes 2 and 3.

In Scheme 4a, azaisobutyronitrile (AIBN) is employed in the cyclization step to form Compound (4–16) which is then transformed as described above to ultimately form Compound (4–19).
SCHEME 4
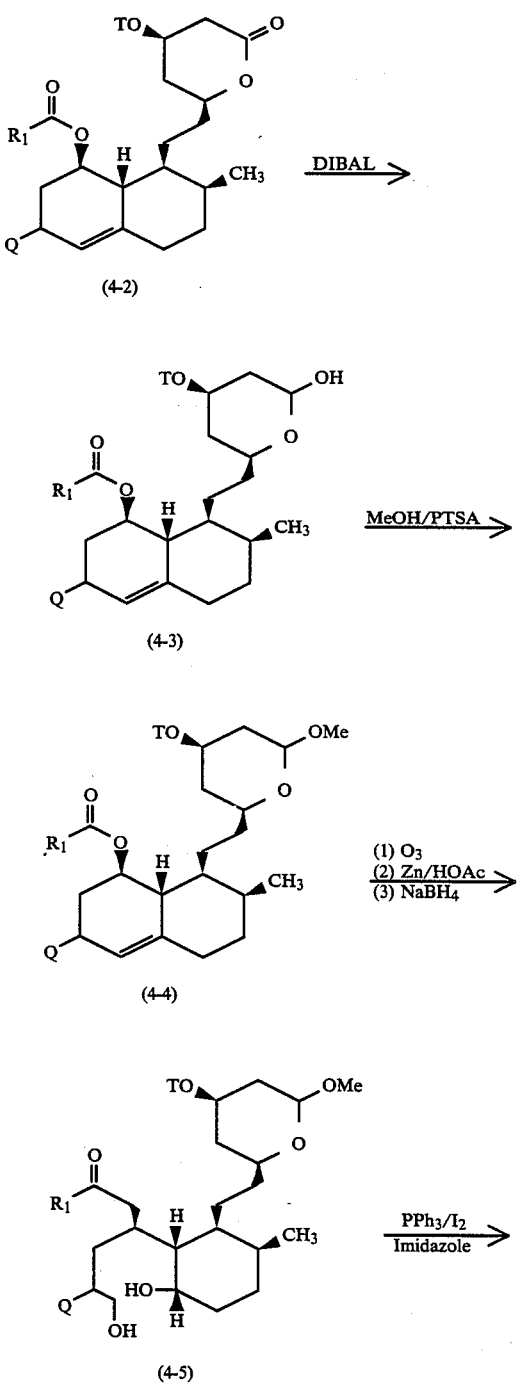
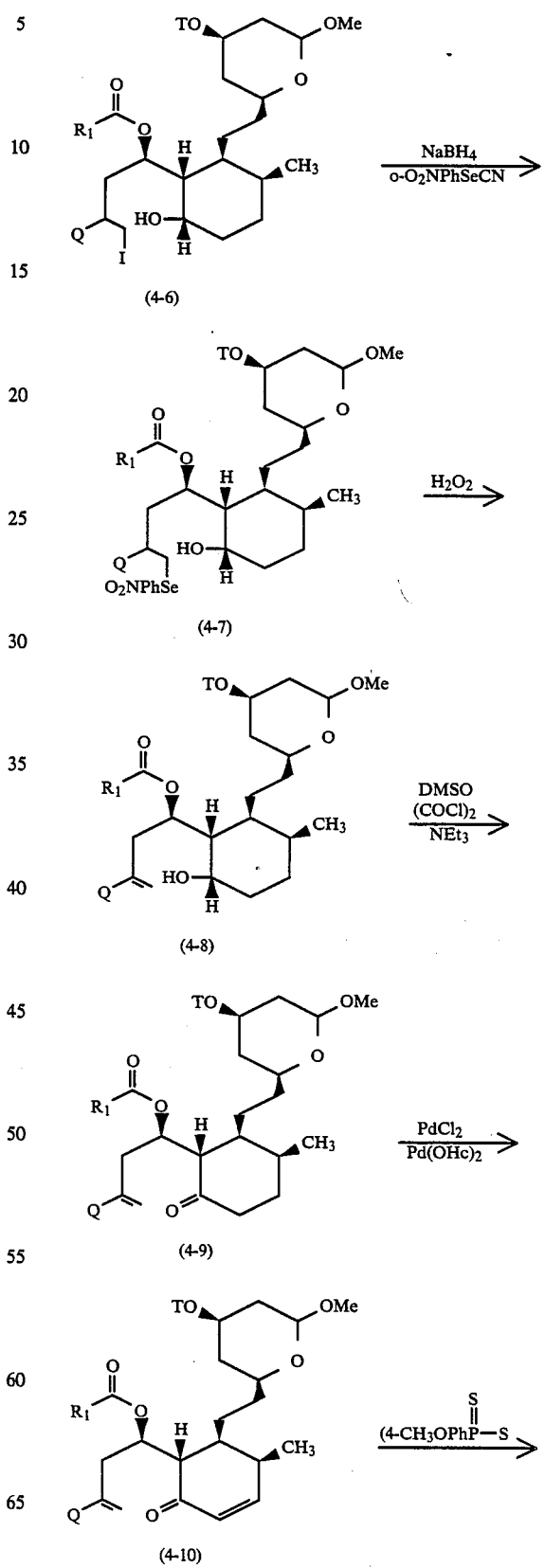

SCHEME 4
-continued
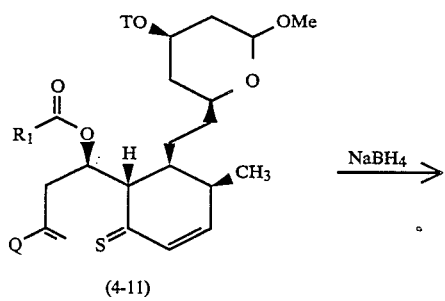
(4-11)
↓ NaBH₄
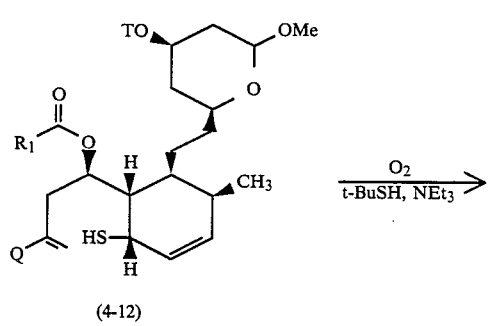
(4-12)
↓ O₂ / t-BuSH, NEt₃
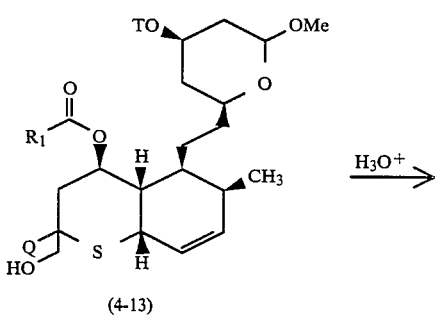
(4-13)
↓ AgCO₃/Celite → n-Bu₄NF → m-CPBA
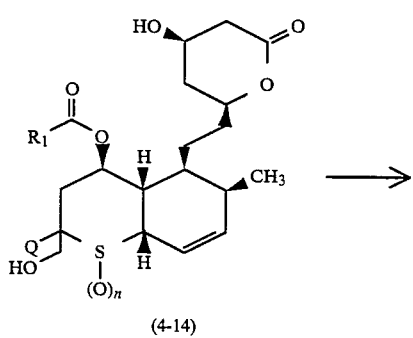
(4-14)
-continued
SCHEME 4
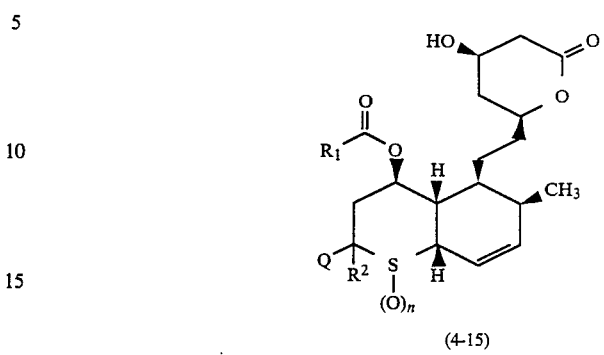
(4-15)
T is a hydroxyl protecting group such as diphenyltert-butylsilyl
SCHEME 4a
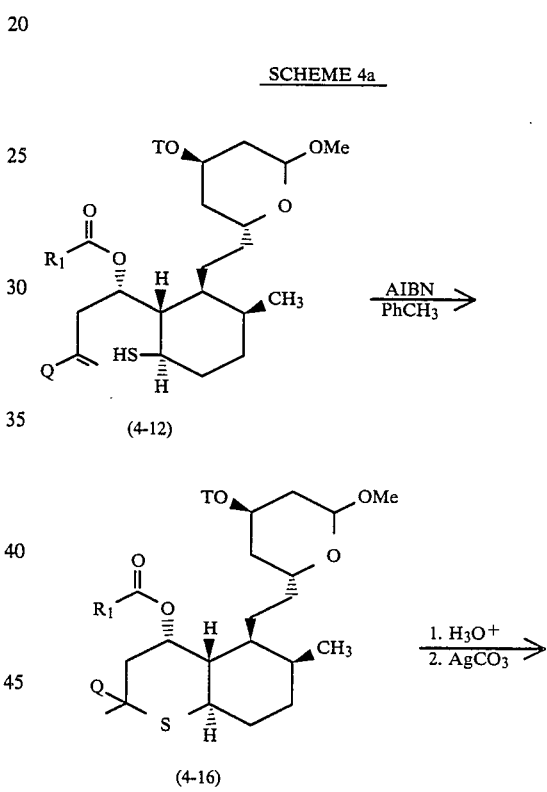
(4-12)
↓ AIBN / PhCH₃
then 1. H₃O⁺  2. AgCO₃
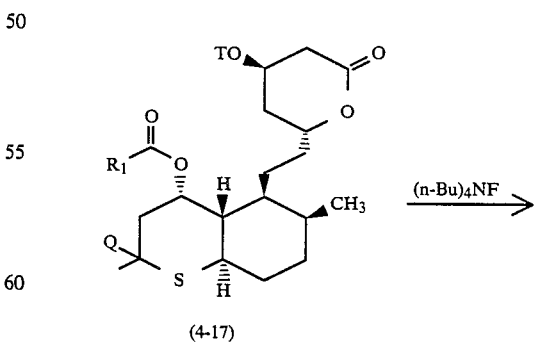
(4-17)
↓ (n-Bu)₄NF -continued
SCHEME 4a

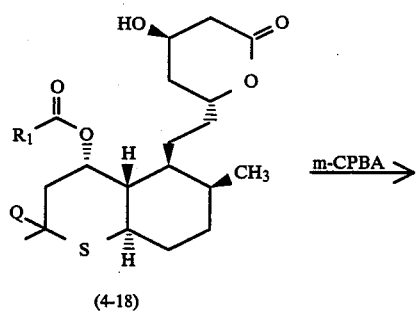

(4-18)

m-CPBA →

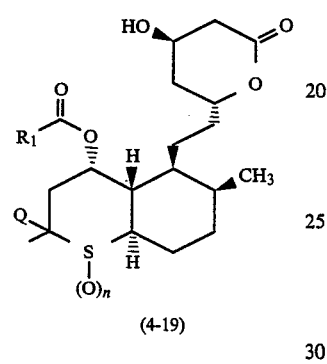

(4-19)

The compounds of formula (I) and (II) wherein A is N-R[13] are prepared following Scheme 5. The conversions in Scheme 5 proceeding to ketone (5-7) are analogous to those described earlier in Schemes 1 and 4. The insertion of nitrogen is accomplished through a reductive amination utilizing benzylamine (BnNH$_2$) and resulting in Compound (5-8). The amine (5-8) is converted to a carbamate (5-9) and then cyclized to the 5-aza analog (5-10) following the procedure of Newcomb et al., Tetrahedron Letters, 26, 5651, (1985) and J. Am. Chem. Soc., 109, 3163 (1987). The hydroxyl protecting is removed employing tetra-butylammonium fluoride and the N-benzyl group replaced by N—H by reaction with H$_2$/Pd/C. The identity and employment of Q in Scheme 5 is analogous to that as previously discussed in Schemes 2 and 3. If desired the 3,4- double bond can be inserted in the aza compounds by reaction of Compound (5-7) with PdCl$_2$/Pd(OAc)$_2$ following an analogous methodology to that expressed in Scheme 4. The enone product is then transformed further to Compound (5-8) etc. following the reactions of Scheme 5.

SCHEME 5

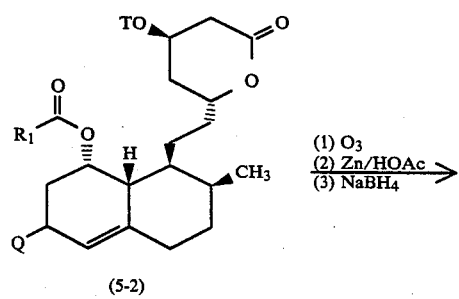

(5-2)

(1) O$_3$
(2) Zn/HOAc →
(3) NaBH$_4$

-continued
SCHEME 5

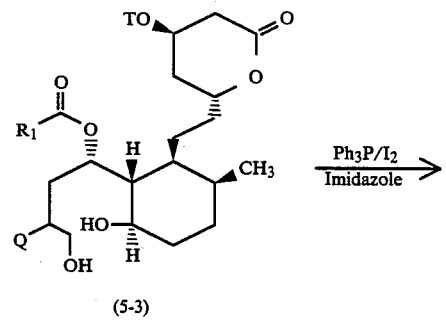

(5-3)

Ph$_3$P/I$_2$ / Imidazole →

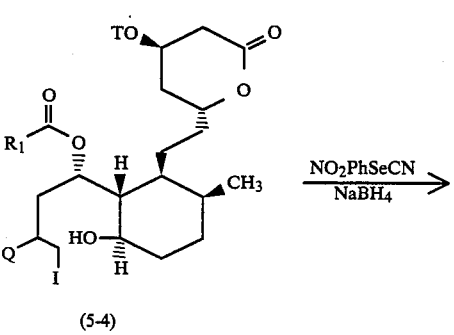

(5-4)

NO$_2$PhSeCN / NaBH$_4$ →

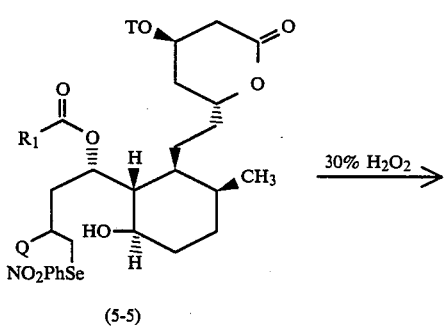

(5-5)

30% H$_2$O$_2$ →

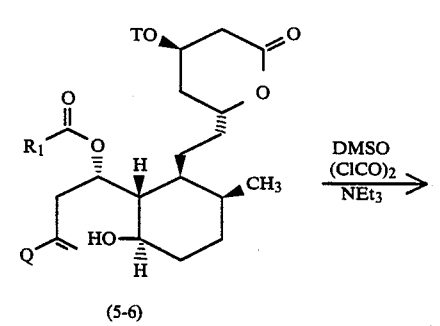

(5-6)

DMSO (ClCO)$_2$ / NEt$_3$ →

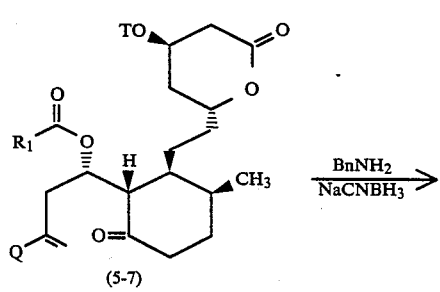

(5-7)

BnNH$_2$ / NaCNBH$_3$ →

-continued
SCHEME 5

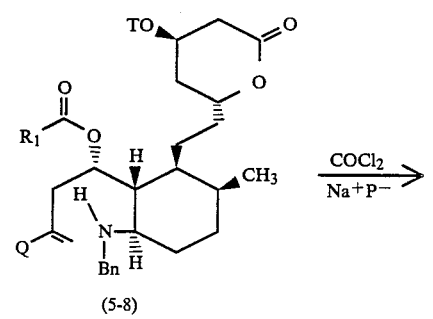

(5-8)

COCl₂ / Na⁺P⁻ →

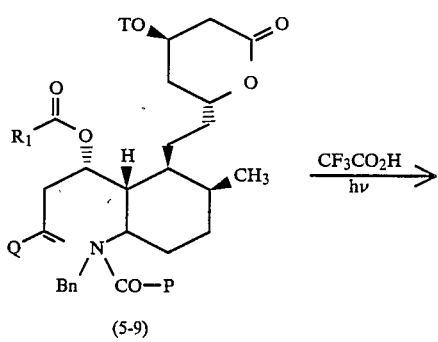

(5-9)

CF₃CO₂H / hν →

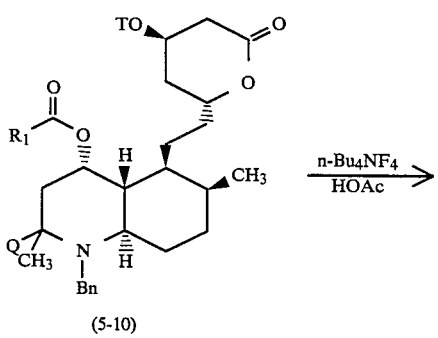

(5-10)

n-Bu₄NF₄ / HOAc →

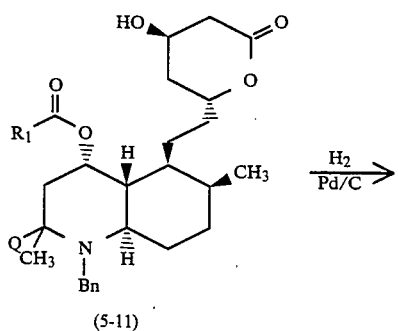

(5-11)

H₂ / Pd/C →

-continued
SCHEME 5

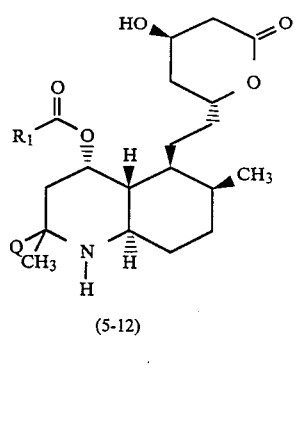

(5-12)

$$P = \text{(structure shown)}$$

T is a hydroxy protecting group such as diphenyltert-butylsilyl
Bn = benzyl

Where the reaction conditions of the above described chemical transformations would be deleterious to the substituents contained in $R_1$, the acetoxy group can be employed as a protecting group which after the insertion of the 5-heteroatom moiety and the elaboration of the 6,6 positions can be removed by hydrolysis to give the 8 hydroxy derivative which can then be acylated according to the general procedures described in U.S. Pat. No. 4,661,483 and co pending U.S. applications Ser. No. 859,513, 859,524, 859,525, 859,520, 859,534 and 859,535 all filed on May 5, 1986. The alkanoyl chloride for preparing the 8-acyloxy moiety can be formed by standard chemical transformations such as substitution with an alkyl moiety or other appropriate electrophile at an acidic C-H site on an available starting material; more specifically the 8-acyloxy moiety can be prepared following the descriptions in the aforementioned co-pending patent applications filed on May 5, 1986.

It may be necessary to protect substituents on the $R_2$, $R_3$ moieties during such chemical transformations as compounds (1-8)→compounds (2-10). Suitable protective groups can be found in *Protective Groups in Organic Synthesis*, Greene, John Wiley & Sons (1981).

Where the product formed by the above described synthetic pathways is not the desired form of that compound, then that product may be subjected to one or more further reactions such as hydrolysis, salification, esterification, acylation, ammonolysis, desilylation or lactonization by conventional methods, as described in more detail hereafter.

Preferred metal salts are salts with alkali metals, such as sodium or potassium, salts with alkaline earth metals, such as calcium, or salts with other metals such as magnesium, aluminum, iron, zinc, copper, nickel or cobalt, of which the alkali metal, alkaline earth metal, magnesium and aluminum salts are preferred, the sodium, calcium and aluminum salts being most preferred.

Preferred amino acids to form amino acid salts are basic amino acids, such as arginine, lysine, $\alpha,\beta$-diaminobutyric acid or ornithine.

Preferred amines to form amine salts include t-octylamine, dibenzylamine, ethylenediamine, morpholine, and tris(hydroxymethyl)aminomethane. Also preferred is ammonia to form the ammonium salt.

Esters are preferably the alkyl esters, such as the methyl, ethyl, propyl, isopropyl, butyl, isobutyl or pentyl esters, of which the methyl ester is preferred. However, other esters such as phenyl $C_{1-5}$alkyl, dimethylamino $C_{1-5}$ alkyl, or acetyl amino-$C_{1-5}$ alkyl may be employed if desired.

Metal salts of the carboxylic acids of formula (II) may be obtained by contacting a hydroxide, carbonate or similar reactive compound of the chosen metal in an aqueous solvent with the carboxylic acid of formula (II). The aqueous solvent employed is preferably water, or it may be a mixture of water with an organic solvent, preferably an alcohol (such as methanol or ethanol), a ketone (such as acetone), an aliphatic hydrocarbon (such as hexane) or an ester (such as ethyl acetate). It is preferred to use a mixture of a hydrophilic organic solvent with water. Such reactions ar normally conducted at ambient temperature but they may, if desired, be conducted with heating or cooling.

Amine salts of the carboxylic acids of formula (II) may be obtained by contacting an amine in an aqueous solvent with the carboxylic acid of formula (II). Suitable aqueous solvents include water and mixtures of water with alcohols (such as methanol or ethanol), ethers (such as diethyl ether and tetrahydrofuran), nitriles (such as acetonitrile) or ketones (such as acetone); it is preferred to use aqueous acetone as the solvent for this reaction. The reaction is preferably carried out at a temperature of ambient or below, more preferably a temperature of from 5° to 10° C. The reaction immediately goes to completion. Alternatively, a metal salt of the carboxylic acid of formula (II) (which may have been obtained as described above) can be dissolved in an aqueous solvent, after which a mineral acid salt (for example the hydrochloride) of the desired amine is added, employing the same reaction conditions as when the amine itself is reacted with the carboxylic acid of formula (II) and the desired product is then obtained by metathesis.

Amino acid salts of the carboxylic acids of formula (II) may be obtained by contacting an amino acid in aqueous solution with the carboxylic acid of formula (II). Suitable aqueous solvents include water and mixtures of water with alcohols (such as methanol or ethanol) or ethers (such as tetrahydrofuran).

Esters, preferably alkyl esters, of the carboxylic acids of formula (II) may be obtained by contacting the carboxylic acid of formula (II) with an appropriate alcohol, preferably in the presence of an acid catalyst, for example a mineral acid (such as hydrochloric acid or sulphuric acid), a Lewis acid (for example boron trifluoride) or an acidic ion exchange resin. The solvent employed for this reaction is not critical, provided that it does not adversely affect the reaction; suitable solvents include the alcohol itself, benzene, chloroform, ethers and the like. Alternatively, the desired product may be obtained by contacting the carboxylic acid of formula (II) with a diazoalkane, in which the alkane moiety may be substituted or unsubstituted. This reaction is usually effected by contacting the acid with an ethereal solution of the diazoalkane. As a further alternative, the ester may be obtained by contacting a metal salt of the carboxylic acid of formula (II) with a halide, preferably an alkyl halide, in a suitable solvent; preferred solvents include dimethylformamide, tetrahydrofuran, dimethylsulfoxide and acetone. Finally, esters may also be obtained from the lactone of formula (I) by reaction with an appropriate alkoxide in an absolute alkanol. All of the reactions for producing esters are preferably effected at about ambient temperature, but, if required by the nature of the reaction system, the reactions may be conducted with heating or cooling.

Lactones of the carboxylic acids of formula (I) may be obtained by lactonizing the carboxylic acids of formula (II) under ordinary conditions known to one skilled in the art.

The intrinsic HMG—CoA reductase inhibition activity of the claimed compounds is measured in the in vitro protocol published in *J. Med. Chem.*, 28, p. 347–358 (1985).

For estimation of relative inhibitory potencies, compactin (i.e., mevastatin) was assigned a value of 100 and the $IC_{50}$ value of the test compound was compared with that of compactin determined simultaneously in the published in vitro protocol.

Representative of the intrinsic HMG-CoA reductase inhibitory activities of the claimed compounds are the following potencies.

| Compound No. | $R_1$ | $R_2$ | $R_3$ | Relative Potency |
|---|---|---|---|---|
| 9 | 2-methyl-2-butyl | $CH_3$ | $CH_3$ | 96 |
| 10 (α-epimer) | 2-methyl-2-butyl | $CH_3$ | $PhSCH_2$ | 258 |
| 11 (β-epimer) | 2-methyl-2-butyl | $PhSCH_2$ | $CH_3$ | 280 |

The compounds of this invention are useful as antihypercholesterolemic agents for the treatment of arteriosclerosis, hyperlipidemia, familial hypercholesterolemia and like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 10 mg to 2000 mg (preferably 10 to 100 mg) which may be given in two to four divided doses. Higher doses may be favorably employed as required.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

Included within the scope of this invention is the method of treating arteriosclerosis, familial hypercholesterolemia or hyperlipidemia which comprises administering to a subject in need of such treatment a nontoxic, therapeutically effective amount of the compounds of formulae (I) or (II) or pharmaceutical compositions thereof.

The following examples illustrate the preparation of the compounds of the formulae (I) and (II) and their incorporation into pharmaceutical compositions and as such are not to be considered as limiting the invention set forth in the claims appended hereto.

EXAMPLE 1

Preparation of
6(R)-[2-[8(S)-(2,2-dimethylbutyryloxy)-2(S)-methyl-5-oxa-6,6-dimethyl-1,2,3,4,4a(R),
7,8,8a(R)-octahydronaphthyl-1(S)]-4(R)-hydroxy-3,4,5,6-tetrahydro-2H-pyran-2-one

Step 1: Preparation of
6(R)-[2-(8(S)-(2,2-dimethylbutyryloxy)-2(S)-methyl-6(R)-methyl-1,2,3,4,6,7,8,8a(S)-octahydronaphthyl-1(S)]ethyl]-4(R)-hydroxy-3,4,5,6-tetrahydro-2H-pyran-2-one(2)

Nitrogen was bubbled through a solution of 50% toluene in absolute ethanol (300 mL) for 5 minutes. Wilkinson's catalyst (5.0 g, 33%/wt.) was added to the solvent and the mixture reduced at room temperature under 50 psi $H_2$ for 1 hour. Simvastatin (15 g, 36 mmol) was added and the resulting pale yellow solution reduced at room temperature under $H_2$ (60 psi) for 40 hours. The mixture was concentrated and the residue heated in toluene (700 mL) at 60° C. in the presence of thiourea (5.0 g, 64 mmol) for 1.5 hours. The mixture was cooled to 0° C. (ice bath), filtered, and concentrated. The residue was diluted with 50% EtOAc/hexane and passed through a pad of silica (~250 cc) to give 2 as a beige solid; mp=128°–129° C. (ethyl/hexane); TLC Rf=0.65 (EtOAc); $^1$H NMR (CDCl$_3$) δ5.36 (bs, 1H), 5.30 (m,1H), 4.58 (m,1H), 4.33 (m,1H), 2.68 (dd,J=17 and 5Hz,1H), 2.68 (m,1H), 2.59 (dd, J=17 and 4Hz,1H), 2.30 1.20 (m), 1.13 (s,3H), 1.12 (s,3H), 1.05 (d, J=7Hz,3H), 0.87 (d, J=7Hz,3H), 0.82 (t, J=7Hz,3H).

Step 2: Preparation of
6(R)-[2-[6(R)-(1(S)-2,2-dimethylbutyryloxy-3(R)-methyl butan-4-ol)2(S)-methyl-5(R)-hydroxycyclohexyl-1(S)]-ethyl]-4(R)-hydroxy-3,4,5,6-tetrahydro-2H-pyran-2-one (3).

Ozone was passed through a red solution of monoene 2 (420 mg, 1.0 mmol) and 1-(p-phenylazophenylazo)-2-naphthol (sudan III) (5 mg) in CH$_3$OH (10 mL) at −78° C. until the red color dissipated (10 minutes). Argon was then bubbled through the solution to remove excess ozone. Addition of zinc (200 mg, 3.0 mmol) and acetic acid (1.0 mL) was followed by removal of the cooling bath and vigorous stirring for 15 minutes. The reaction mixture was diluted with ethyl acetate and filtered through celite. The filtrate was washed with H$_2$O and brine, dried (MgSO$_4$), and concentrated. The crude keto-aldehyde was immediately dissolved in THF/H$_2$O (10:1, 8.0 mL), cooled to 0° C., and treated with NaBH$_4$ (100 mg, 3.0 mmol) in 2 portions. After 20 minutes the reaction mixture was diluted with ethyl acetate, washed with H$_2$O, and brine, dried (MgSO$_4$), and concentrated. Flash chromatography (silica, EtOAc) gave the desired product as an oil.

$^1$H NMR (CDCl$_3$): δ5.55 (m, 1H), 4.72 (m, 1H), 4.38 (m, 1H), 3.61 (dd, 1H, J=10 and 3Hz), 3.44 (dd, 1H, J=10 and 3Hz), 3.39 (m, 1H), 2.73 (dd, 1H, J=15 and 3Hz), 2.63 (m, 1H), 2.01-1.20 (m), 1.15 (s, 6H), 0.96 (d, 3H, J=4Hz), 0.85 (t, 3H, J=6Hz) 0.83 (d, 3H, J=7Hz).

Elemental Anal. C$_{25}$H$_4$O$_7$·1.OH$_2$O Calc'd: C, 63.26; H, 9.77. Found: C, 63.13; H, 9.51.

Step 3: Preparation of
6(R)-[2-[6(R)-(1(S)-2,2-dimethylbutyryloxy-3(R)-methyl-4-p-toluenesulfonyl-butane)-2(S)-methyl-5(R)-hydroxycyclohexyl 1(S)]ethyl]-4(R)-hydroxy-3,4,5,6-tetrahydro-2H-pyran-2-one (4)

To a stirred solution of the triol 3 (100 mg, 0.22 mmol), pyridine (71 ml, 1.0 mmol), and dry CH$_2$Cl$_2$ (1.1 mL) at 0° C. was added p-toluenesulfonyl chloride (50 mg, 0.26 mmol). After 5 minutes the cooling bath was removed and the reaction stirred overnight. The reaction mixture was diluted with ethyl acetate, washed with H$_2$O and brine, dried (MgSO$_4$), and concentrated. Flash chromatography (silica, 8% acetone/CH$_2$Cl$_2$) furnished the desired product as a colorless foam.

$^1$H NMR (CDCl$_3$): δ7.75 (d, 2H, J=8Hz), 7.31 (d, 2H, J=8Hz), 5.45 (m, 1H), 4.66 (m, 1H), 4.33 (m, 1H), 4.02 (dd, 1H, J=10 and 5Hz), 3.79 (dd, 1H, J=10 and 4Hz), 3.32 (m, 1H), 2.63 (m, 2H), 2.40 (S, 3H), 2.00-1.20 (m), 1.10 (S, 6H), 0.90 (d, 3H, J=7Hz), 0.80 (d, 3H, J=7Hz), 0.78 (t, 3H, J=7Hz).

Step 4: Preparation of
6(R)-[2-[6(R)-(1(S)-2,2-dimethylbutyryloxy 3(R)-methyl-4-iodo-butane)-2(S)-methyl-5(R)-hydroxy-cyclohexyl-1(S)]ethyl]-4(R)-hydroxy 3,4,5,6-tetrahydro-2-H-pyran-2-one (5)

A stirred mixture of the tosylate 4 (0.80 g, 1.3 mmol), NaI (1.2 g, 7.8 mmol), and acetone (8.0 mL) was heated to reflux for 2.0 h. The cooled reaction mixture was diluted with ether, washed sequentially with H$_2$O, 10% Na$_2$SO$_3$, and brine, dried (MgSO$_4$), and concentrated. Flash chromatography (silica, ether) gave the desired product 5 as a colorless oil.

$^1$H NMR (CDCl$_3$): δ5.44 (m, 1H), 4.68 (m, 1H), 4.37 (m, 1H), 3.40 (m, 1H), 3.32 (dd, 1H, J=15 and 5Hz), 3.25 (dd, 1H, J=15 and 3Hz), 2.70 (dd, 1H, J=15 and 4Hz), 2.61 (m, 1H), 2.00-1.28 (m), 1.13 (S, 6H), 0.98 (d, 3H, J=7Hz), 0.83 (t, 3H, J=7Hz), 0.82 (d, 3H, J=7Hz).

Step 5: Preparation of
6(R)-[2-[6(R)-(1(S)-2,2-dimethylbutyryloxy-3(R)-methyl-4-o-nitrophenylseleno-butane)-2(S)-methyl-5(R)-hydroxy-cyclohexyl-1(S)]ethyl]-e(R)-hydroxy-3,4,5,6-tetrahydro-2H-pyran-2-one (6)

A stirred solution of the iodide 5 (208 mg, 0.37 mmol), 2-nitrophenyl selenocyanate (167 mg, 0.75 mmol), and dry DMF (2.0 ml) was degassed, cooled to 0° C. and then treated with NaBH$_4$ (14 mg, 0.37 mmol). After 10 minutes the cooling bath was removed and the mixture stirred for 2.0 hours. The reaction mixture was diluted with ethyl acetate, washed with H$_2$O and brine, dried (MgSO$_4$), and concentrated. Flash chromatography (silica, 70% EtOAc/hexane) afforded the desired product 6 as a yellow oil.

$^1$H NMR (CDCl$_3$): δ8.23 (m, 1H), 7.54 (m, 2H), 7.28 (m, 1H), 5.60 (m, 1H), 4.67 (m, 1H), 4.38 (m, 1H), 3.35 (m, 1H), 3.05 (dd, 1H, J=11 and 4Hz), 2.80 (dd, 1H J=11 and 4Hz), 2.68 (m, 2H), 2.00-1.30 (m), 1.55 (S 3H), 1.54 (d, 3H), 1.16 (d, 3H), 1.14 (S, 3H), 0.81 (t J=6Hz).

Step 6: Preparation of 6(R)-[2-[6(R)-(1(S)-2,2-dimethylbutyryloxy-3-methyl-3-butene)-2(S)-methyl-5-(R)-hydroxy-cyclohexyl-1(S)]ethyl]-4(R)-hydroxy-3,4,5,6-tetrahydro-2-H-pyran-2-one (7)

To a stirred solution of the selenide 6 (250 mg, 0.33 mmol) in THF (3 ml) at 0° C. was added 30% $H_2O_2$ (75 μl, 0.66 mmol) dropwise. After 5 minutes the cooling bath was removed and the reaction mixture stirred overnight. The orange solution was diluted with ethyl acetate, washed with sat. $NaHCO_3$ and brine, dried ($MgSO_4$), and concentrated. Flash chromatography (silica, ether) furnished the desired product 7 as an oil.

$^1$H NMR (CDCl$_3$): δ5.48 (m, 1H), 4.78(d,2H,J=5Hz) 4.70 (m, 1H), 4.40 (m, 1H), 3.43 (m, 1H), 2.74 (dd, 1H, J=16 and 3Hz), 2.64 (m, 1H), 2.55-2.27 (m, 2H), 2.05-1.24 (m), 1.15 (s, 6H), 0.85 (d, 3H, J=7Hz), 0.84 (t, 3H, J=7Hz).

Elemental Anal. $C_{25}H_{42}O_6 \cdot 0.5\ H_2O$: Calc'd: C, 67.08; H, 9.68. Found: C, 66.91; H, 9.61.

Step 7: (a) Preparation of 6(R)-[2-[8(S)-(2,2-dimethylbutyryloxy)-2(S) methyl-5-oxa-6(S)-(iodomethyl, methyl)-1,2,3,4,4a(R), 7,8,8a-(R)-octahydronaphthyl-1(S)]ethyl]4(R)-hydroxy-3,4,5,6-tetrahydro-2H-pyran-2-one(8a) (b) 6(R)-[2-[8(S)-(2,2-dimethylbutyryloxy)-2(S)-methyl-5-oxa-6(R)-(iodomethyl, methyl)-1,2,3,4,4a(R),7,8,8a(R)-octahydronaphthyl-1(S)ethyl]-4(R)-hydroxy-3,4,5,6-tetrahydro-2H-pyran-2-one (8b)

A stirred mixture of the olefin 7 (149 mg, 0.34 mmol), $NaHCO_3$ (115 mg, 1.3 mmol), and $CH_2Cl_2$ (3.4 mL) at 0° C. was treated with iodine (173 mg, 0.68 mmol) in one portion. After 15 minutes the dark red mixture was diluted with ethyl acetate, washed sequentially with $H_2O$, 10% $Na_2SO_3$, and brine, dried ($MgSO_4$), and concentrated. Flash chromatography (silica, ether) afforded the crude product 8 (1:1 mixture of epimers) as a red oil.

$^1$H NMR of mixture (CDCl$_3$): δ5.20 (m, 1H), 4.58 (m, 1H), 4.35 (m, 1H), 3.79 (d, 0.5H, J=8Hz), 3.61 (m, 0.5H), 3.48 (m, 0.5H), 3.34 (d, 0.5H, J=8Hz), 3.17 (m, 1H), 2.71 (dd, 1H, J=15 and 5Hz), 2.30-1.10 (m), 0.84 (m, 6H).

Step 8: 6(R) [2-[8(S)-(2,2-dimethylbutyryloxy)-2(S)-methyl-5-oxa-6,6-dimethyl-1,2,3,4,4a(R),7,8,8a(R)-octahydronaphthyl-1(S)]ethyl]-4(R)-hydroxy-3,4,5,6-tetrahydro-2H-pyran-2-one (9)

A stirred mixture of iodides 8 (153 mg, 0.27 mmol), tributyltin hydride (237 μl, 0.81 mmol), and azaisobutyronitrile (AIBN) (2 mg) in degassed toluene (1.4 ml) was heated at 80° C. for 4.0 hours. The cooled reaction mixture was concentrated to dryness. The residue was dissolved in $CH_3CN$ (10 ml) and washed with hexanes (10×).

The hexane washes, containing tin byproducts, were decanted away from the acetonitrile. The acetonitrile was evaporated and the residue subjected to flash chromatography (silica, 20% EtOAc/$CH_2Cl_2$) to furnish the crude product. The crude material was purified by preparative plate (0.5 mm, silica, 20% EtOAc/$CH_2Cl_2$) chromatography to yield the desired product 9 as a colorless oil.

$^1$H NMR (CDCl$_3$): δ5.20 (m, 1H), 4.59 (m, 1H), 4.37 (m, 1H), 3.63 (m, 1H), 2.73 (dd, 1H, J=16 and 4Hz), 2.61 (m, 1H), 2.00-1.15 (m), 1.32 (S, 3H), 1.27 (S, 3H), 1.25 (S, 3H), 1.24 (S, 3H), 0.87 (d, 3H, J=6Hz), 0.84 (t, 3H, J=7Hz).

Elemental Anal. $C_{25}H_{42}O_6 \cdot 1.0H_2O$: Calc'd: C, 67.23; H, 9.93. Found: C, 66.87; H, 9.61.

EXAMPLE 2

Preparation of 6(R)-[2-[8(S)-(2,2-dimethylbutyryloxy)-2(S)-methyl-5-oxa-6(S)-(phenylthiomethyl, methyl)-1,2,3,4,4a(R),7,8,8a(R)-octahydronaphthyl-1(S)]ethyl]4(R)-hydroxy 3,4,5,6-tetrahydro-2H-pyran-2-one. (10) (R) 6[2-[8(S)-(2,2-dimethylbutyryloxy)-2(S)-methyl-5-oxa-6(R)-(phenylthiomethyl, methyl)-1,2,3,4,4a(R),7,8,8a(R)-octahydronaphthyl-1(S)]ethyl]-4(R)-hydroxy-3,4,5,6-tetrahydro-2H-pyran-2-one (11)

Steps 1–7 were repeated following the procedure of Example 1.

Step 8: Preparation of 6(R)-[2-[8(S)-(2,2-dimethylbutyryloxy)-2(S)-methyl-5-oxa-6(S)-(phenylthiomethyl, methyl)-1,2,3,4,4a(R),7,8,8a(R)-octahydronaphthyl-1-(S)]ethyl]-4(R)-hydroxy-3,4,5,6-tetrahydro-2H-pyran-2-one (10) 6(R)-[2-[8(S)-(2,2-dimethylbutyryloxy)-2(S)-methyl-5-oxa-6(R)-(phenylthiomethyl, methyl)-1,2,3,4,4a(R),7,-8,8a(R)-octahydronaphthyl-1(S)]ethyl]-4-(R)-hydroxy 3,4,5,6-tetrahydro-2H-pyran-2-one (11)

A degassed solution of iodides 8 (120 mg, 0.21 mmol), thiophenol (110 μl, 1.0 mmol), 1,8-diazabicyclo[5.4.0]undec-7-ene (150 μl, 1.0 mmol), and dry DMF was heated at 80° C. for 4.0 hours. The cooled reaction mixture was diluted with ether, washed with $H_2O$ (2×) and brine, dried ($MgSO_4$), and concentrated. Flash chromatography (silica, 80% EtOAc/hexane) gave a 1:1 mixture of epimers as a colorless oil. Separation of the epimers was accomplished by preparative plate chromatography (0.5 mm silica, 65% EtOAc/benzene) to furnish the faster moving α-epimer 10 and the slower moving β-epimer 11 as colorless oils.

α epimer: $^1$H NMR (CDCl$_3$): δ7.40-7.10 (m, 5H), 5.23 (bs, 1H), 4.56 (m, 1H), 4.34 (m, 1H), 3.62 (m, 1H), 3.06 (d, 1H, J=13Hz), 2.95 (d, 1H, J=13Hz), 2.70 (dd, 1H, J=15 and 5Hz), 2.58 (dd, 1H, J=15 and 2Hz), 2.14 (m, 1H), 2.00-1.14 (m), 1.40 (S, 3H), 1.17 (S, 3H), 1.16 (S, 3H), 0.84 (d, 3H, J=7Hz), 0.83 (t, 3H, J=7Hz).

β-epimer: $^1$H NMR (CDCl$_3$): δ7.40-7.10 (m, 5H), 5.20 (m, 1H), 4.56 (m, 1H), 4.33 (m, 1H), 3.64 (d, 1H, J=12Hz), 3.48 (m, 1H), 3.04 (d, 1H, J=12Hz), 2.70 (dd, 1H, J=15 and 5Hz), 2.58 (m, 1H), 2.22-1.10 (m), 1.29 (S, 3H), 1.13 (S, 3H), 1.12 (S, 3H), 0.83 (d, 3H, J=7Hz), 0.82 (t, 3H, J=7Hz).

EXAMPLE 3

Preparation of 6(R) [8(S)-(2-methylbutyryloxy)-2(S)-methyl-5-oxa-6,6-dimethyl-1,2,3,4,4a(R),7,8,8 a(R)-octahydronaphthyl-1(S)ethyl]-4(R) hydroxy-3,4,5,6-tetrahydro-2H-pyran-2-one (12)

Utilizing the general procedure of Example 1 but substituting 6(R)-[2-8(S)-(2-methylbutyryloxy)-2(S)- methyl-6(R)-methyl 1,2,6,7,8,8a(R)-hexahydro-naphthyl-1(S)]ethyl]-4(R)-hydroxy-3,4,5,6-tetrahydro-2H-pyran-2-one, for the starting polyhydronaphthyl moiety, the titled compound is prepared.

EXAMPLES 4–33

Utilizing the general procedures in Examples 1-2 and, where a is a double bond, the modifications of Scheme 3, the following compounds of formula I wherein $R_1$=2-methyl-2-butyl and A=O are prepared from the appropriately substituted starting materials.

| Compound No. | $R_2$ | $R_3$ | a |
|---|---|---|---|
| 13 | $CH_2OH$ | $CH_3$ | sb |
| 14 | $CH_3$ | $CH_2OH$ | sb |
| 15 | $CH_2OH$ | $CH_2SPh$ | sb |
| 16 | $CH_2SPh$ | $CH_2OH$ | sb |
| 17 | $CH_3$ | $CH_3$ | db |
| 18 | $CH_2OH$ | $CH_3$ | db |
| 19 | $CH_3$ | $CH_2OH$ | db |
| 20 | $CH_2OH$ | $CH_2SPh$ | db |
| 21 | $CH_2SPh$ | $CH_2OH$ | db |
| 22 | $CH_3$ | $CH_2SPh$ | db |
| 23 | $CH_2SPh$ | $CH_3$ | db |
| 24 | H | $CH_3$ | sb |
| 25 | $CH_3$ | H | sb |
| 26 | $CH_2OH$ | H | sb |
| 27 | H | $CH_2OH$ | sb |
| 28 | $CH_2OCH_3$ | $CH_3$ | sb |
| 29 | $CH_3$ | $CH_2OCH_3$ | sb |
| 30 | $CH_2OC(O)NHPh$ | $CH_3$ | sb |
| 31 | $CH_3$ | $CH_2OC(O)NHPh$ | sb |
| 32 | $CH_2SCH_2Ph$ | H | sb |
| 33 | H | $CH_2SCH_2Ph$ | sb |
| 34 | $CH_2NHC(O)CH_3$ | $CH_3$ | sb |
| 35 | $CH_3$ | $CH_2NHC(O)CH_3$ | sb |
| 36 | H | $CH_2NHCH_2Ph$ | sb |
| 37 | $CH_2NHCH_2Ph$ | H | sb |
| 38 | $CH_2P(O)(OCH_2Ph)_2$ | H | sb |
| 39 | H | $CH_2P(O)(OCH_2Ph)_2$ | sb |
| 40 | $CH_2P(O)(CH_3)_2$ | $CH_3$ | sb |
| 41 | $CH_3$ | $CH_2P(O)(CH_3)_2$ | sb | sb = single bond
db = double bond

EXAMPLE 34

Preparation of Ammonium Salts of Compounds II

The lactone (1.0 mmol) from Example 1, Step 8, is dissolved with stirring in 0.1N NaOH (1.1 mmol) at ambient temperature. The resulting solution is cooled and acidified by the dropwise addition of 1N HCl. The resulting mixture is extracted with diethyl ether and the extract washed with brine and dried (Mg SO4). The MgSO4 is removed by filtration and the filtrate saturated with ammonia (gas) to give a gum which solidified to provide the ammonium salt.

EXAMPLE 35

Preparation of Alkali and Alkaline Earth Salts of Compounds II

To a solution of 44 mg of lactone from Example 1, Step 8, in 2 ml of ethanol is added 1 ml of aqueous NaOH (1 equivalent). After one hour at room temperature, the mixture is taken to dryness in vacuo to yield the desired sodium salt.

In like manner, the potassium salt is prepared using one equivalent of potassium hydroxide, and the calcium salt, using one equivalent of CaO.

EXAMPLE 36

Preparation of Ethylenediamine Salts of Compounds II

To a solution of 0.50 g of the ammonium salt from Example 34 in 10 ml of methanol is added 0.04 ml of ethylenediamine. The methanol is stripped off under vacuum to obtain the desired ethylenediamine salt.

EXAMPLE 37

Preparation of Tris(hydroxymethyl)aminomethane Salts of Compounds II

To a solution of 202 mg of the ammonium salt from Example 34 in 5 ml of methanol is added a solution of 50 mg of tris(hydroxymethyl) aminomethane in 5 ml of methanol. The solvent is removed in vacuo to afford the desired tris(hydroxymethyl)aminomethane salt.

EXAMPLE 38

Preparation of L-Lysine Salts of Compounds II

A solution of 0.001 mole of L-lysine and 0.0011 mole of the ammonium salt from Example 34 in 15 ml of 85% ethanol is concentrated to dryness in vacuo to give the desired L-lysine salt.

Similarly prepared are the L-arginine, L-ornithine, and N-methylglucamine salts.

EXAMPLE 39

Preparation of Tetramethylammonium Salts of Compounds II

A mixture of 68 mg of ammonium salt from Example 34 in 2 ml of methylene chloride and 0.08 ml of 24% tetramethylammonium hydroxide in methanol is diluted with ether to yield the desired tetramethylammonium salt.

EXAMPLE 40

Preparation of Methyl Esters of Compounds II

To a solution of 400 mg of lactone from Example 1, Step 8, in 100 ml of absolute methanol is added 10 ml 0.1M sodium methoxide in absolute methanol. This solution is allowed to stand at room temperature for one hour, then is diluted with water and extracted twice with ethyl acetate. The organic phase is separated, dried (Na2SO4), filtered and evaporated in vacuo to yield the desired methyl ester.

In like manner, by the use of equivalent amounts of propanol, butanol, isobutanol, t-butanol, amylalcohol, isoamylalcohol, 2,2-dimethylaminoethanol, benzylalcohol, phenethanol, 2-acetamidoethanol and the like, the corresponding esters are obtained.

EXAMPLE 41

Preparation of Free Dihydroxy Acids

The sodium salt of the compound II from Example 35 is dissolved in 2 ml of ethanol-water (1:1; v:v) and added to 10 ml of 1N hydrochloric acid from which the dihydroxy acid is extracted with ethyl acetate. The organic extract is washed once with water, dried (Na2SO4), and evaporated in vacuo with a bath temperature not exceeding 30° C. The dihydroxy acid derivative derived slowly reverts to the corresponding, parent lactone on standing. The compound can be maintained in the dihydroxy acid form by increasing the pH above 7.0.

EXAMPLE 42

As a specific embodiment of a composition of this invention, 20 mg of lactone from Example 1, Step 8, is formulated with sufficient finely divided lactose to provide a total amount of 580 to 590 mg to fill a size 0, hard gelatin capsule.

What is claimed is:

1. A compound represented by the following structural formulae (I) and (II):

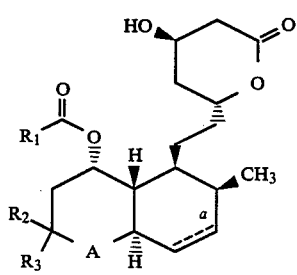

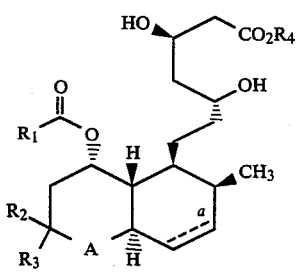

wherein:

A is O or $S(O)_n$ or $N-R_{13}$;

n is 0 to 2;

$R_1$ is selected from:
(1) $C_{1-10}$ alkyl;
(2) substituted $C_{1-10}$ alkyl in which one or more substitutent(s) is selected from
  (a) halogen,
  (b) hydroxy,
  (c) $C_{1-10}$ alkoxy,
  (d) $C_{1-5}$ alkoxycarbonyl,
  (e) $C_{1-5}$ acyloxy,
  (f) $C_{3-8}$ cycloalkyl,
  (g) phenyl,
  (h) substituted phenyl in which the substituents are X and Y,
  (i) $C_{1-10}$ alkylS(O)$_n$ in which n is 0 to 2,
  (j) $C_{3-8}$ cycloalkylS(O)$_n$,
  (k) phenylS(O)$_n$,
  (l) substituted phenylS(O)$_n$ in which the substituents are X and Y, and
  (m) oxo;
(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is selected from
  (a) $C_{1-10}$ alkyl,
  (b) substituted $C_{1-10}$ alkyl in which the substituent is selected from
    (i) halogen,
    (ii) hydroxy,
    (iii) $C_{1-10}$ alkoxy,
    (iv) $C_{1-5}$ alkoxycarbonyl,
    (v) $C_{1-5}$ acyloxy,
    (vi) phenyl,
    (vii) substituted phenyl in which the substituents are X and Y
    (viii) $C_{1-10}$ alkylS(O)$_n$,
    (ix) $C_{3-8}$ cycloalkylS(O)$_n$,
    (x) phenylS(O)$_n$,
    (xi) substituted phenylS(O)$_n$ in which the substituents are X and Y, and
    (xii) oxo,
  (c) $C_{1-10}$ alkylS(O)$_n$,
  (d) $C_{3-8}$ cycloalkylS(O)$_n$,
  (e) phenylS(O)$_n$,
  (f) substituted phenylS(O)$_n$ in which the substituents are X and Y,
  (g) halogen,
  (h) hydroxy,
  (i) $C_{1-10}$ alkoxy,
  (j) $C_{1-5}$ alkoxycarbonyl,
  (k) $C_{1-5}$ acyloxy,
  (l) phenyl, and
  (m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(17) $R_5S$ in which $R_5$ is selected from
  (a) $C_{1-10}$ alkyl,
  (b) phenyl, and
  (c) substituted phenyl in which the substituents are X and Y;

$R_2$ and $R_3$ are independently selected from:
(1) hydrogen;
(2) $C_{1-10}$ alkyl; and
(3) substituted $C_{1-10}$ alkyl in which one or more substituents is selected from
  (a) halogen,
  (b) hydroxy,
  (c) $C_{1-10}$ alkoxy,
  (d) $C_{1-5}$ alkoxycarbonyl,
  (e) $C_{1-5}$ alkylacyloxy,
  (f) phenylacyloxy,
  (g) phenoxycarbonyl,
  (h) phenyl $C_{1-5}$ alkylacyloxy,
  (i) phenyl $C_{1-5}$ alkyloxy,
  (j) amino,
  (k) $C_{1-5}$ alkylamino,
  (l) di($C_{1-5}$ alkyl)amino,
  (m) phenylamino,
  (n) substituted phenylamino in which the substituents are X and Y; ·
  (o) phenyl $C_{1-5}$ alkylamino,
  (p) substituted phenyl $C_{1-5}$ alkylamino in which the substituents are X and Y,
  (q) $C_{3-8}$ cycloalkyl,
  (r) phenyl,
  (s) substituted phenyl in which the substituents are X and Y,
  (t) phenylS(O)$_n$, (u) substituted phenyl S(O)$_n$ in which the substituents are X and Y,
(v) phenyl C$_{1-5}$alkyl S(O)$_n$,
(w) C$_{1-5}$alkylS(O)$_n$;
(x) phenylaminoacyloxy,
(y) C$_{1-5}$alkylaminoacyloxy,
(z) C$_{1-5}$ alkylacylamino,
(cc) phenylC$_{1-5}$ alkylacylamino;
(4) R$_2$ and R$_3$ together with the carbon atom to which they are attached form a C$_{3-8}$ carbo-cyclic ring;
R$_4$ is selected from:
(1) hydrogen;
(2) C$_{1-5}$ alkyl;
(3) substituted C$_{1-5}$ alkyl in which the substituent is selected from
(a) phenyl,
(b) dimethylamino, and
(c) acetylamino, and
(4) 2,3-dihydroxypropyl;
R$_{13}$ is selected from:
(1) hydrogen;
(2) C$_{1-5}$ alkyl;
(3) substituted C$_{1-5}$ in which the substituent is selected from:
(a) phenyl,
(b) dimethylamino, and
(c) acetylamino, and
(d) hydroxy, provided that hydroxy is substituted only at C-2, C-3, C-4 or C-5; and
(e) C$_{1-5}$ alkoxy;
(4) C$_{1-5}$ alkylcarbonyl;
(5) C$_{1-5}$ alkyloxycarbonyl;
(6) C$_{1-5}$ alkylaminocarbonyl;
X and Y independently are hydrogen, halogen, trifluoromethyl, C$_{1-3}$ alkyl, nitro, cyano or group selected from:
(1) R$_6$O(CH$_2$)$_m$ in which m is 0 to 3 and R$_6$ is hydrogen, C$_{1-3}$alkyl or hydroxy-C$_{2-3}$alkyl;
(2)

in which R$_7$ is hydrogen, C$_{1-3}$alkyl, hydroxy-C$_{2-3}$alkyl, phenyl, naphthyl, amino-C$_{1-3}$alkyl, C$_{1-3}$alkylamino-C$_{1-3}$alkyl, di(C$_{1-3}$ alkyl)amino-C$_{1-3}$alkyl, hydroxy-C$_{2-3}$ alkylamino-C$_{1-3}$alkyl or di(hydroxy-C$_{2-3}$alkyl) amino-C$_{1-3}$alkyl; provided that in

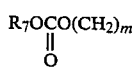

R$_7$ is not H;
(3)

in which R$_8$ is hydrogen, C$_{1-3}$alkyl, hydroxy-C$_{2-3}$ alkyl, C$_{1-3}$alkoxy-C$_{1-3}$alkyl, phenyl or naphthyl;
(4) R$_9$R$_{10}$N(CH$_2$)$_m$,

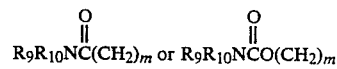

in which R$_9$ and R$_{10}$ independently are hydrogen, C$_{1-3}$ alkyl, hydroxy-C$_{2-3}$ alkyl;
(5) R$_{11}$S(O)$_n$(CH$_2$)$_m$ in which R$_{11}$ is hydrogen, C$_{1-3}$ alkyl, amino, C$_{1-3}$ alkylamino or di(C$_{1-3}$alkyl)amino;
a is a single bond or a double bond;
halogen is F or Cl;
or a pharmaceutically acceptable salt thereof.

2. A compound of claim 1 wherein:
A is O or S(O)$_n$;
R$_2$ and R$_3$ are independently selected from:
(1) hydrogen;
(2) C$_{1-10}$ alkyl;
(3) substituted C$_{1-10}$ alkyl in which one or more substituents is selected from:
(a) halogen,
(b) hydroxy,
(c) amino;
(4) CH$_2$R$_{12}$ in which R$_{12}$ is selected from:
(a) C$_{1-5}$ alkoxy,
(b) C$_{1-5}$ alkoxycarbonyl,
(c) C$_{1-5}$ alkylacyloxy,
(d) phenylacyloxy,
(e) phenoxycarbonyl,
(f) phenylC$_{1-5}$alkylacyloxy,
(g) phenylC$_{1-5}$alkoxy,
(h) C$_{1-5}$alkylamino,
(i) di(C$_{1-5}$alkyl)amino,
(j) phenylamino,
(k) substituted phenylamino in which the substituents are X and Y,
(l) phenyl C$_{1-5}$alkylamino,
(m) substituted phenyl C$_{1-5}$ alkyl amino in which the substituents are X and Y,
(n) C$_{3-8}$ cycloalkyl,
(o) phenyl,
(p) substituted phenyl in which the substituents are X and Y,
(q) phenylS(O)$_n$
(r) substituted phenylS(O)$_n$ in which the substituents are X and Y,
(s) phenyl C$_{1-5}$ alkylS(O)$_n$,
(t) C$_{1-5}$ alkylS(O)$_n$,
(u) phenylaminoacyloxy,
(v) C$_{1-5}$ alkylaminoacyloxy,
(w) C$_{1-5}$ alkylacylamino;
(z) phenylC$_{1-5}$alkylacylamino;
(5) R$_2$ and R$_3$ together with the carbon atom to which they are attached from a C$_{3-8}$ carbocyclic ring.

3. A compound of claim 2 wherein:
R$_1$ is selected from:
(1) C$_{1-10}$ alkyl;
(2) substituted C$_{1-10}$ alkyl in which one or more substituent(s) is selected from
(a) halogen,
(b) hydroxy,
(c) C$_{1-10}$ alkoxy,
(d) C$_{1-5}$ alkoxycarbonyl,
(e) C$_{1-5}$ acyloxy,
(f) C$_{3-8}$ cycloalkyl,
(g) phenyl, (h) substituted phenyl in which the substituents are X and Y, and
(i) oxo;
(3) $C_{3-8}$ cycloalkyl;
(4) substituted $C_{3-8}$ cycloalkyl in which one substituent is selected from
  (a) $C_{1-10}$ alkyl,
  (b) substituted $C_{1-10}$ alkyl in which the substituent is selected from
    (i) halogen,
    (ii) hydroxy,
    (iii) $C_{1-10}$ alkoxy,
    (iv) $C_{1-5}$ acyloxy,
    (v) $C_{1-5}$ alkoxycarbonyl,
    (vi) phenyl,
    (vii) substituted phenyl in which the substituents are X and Y, and
    (viii) oxo,
  (c) halogen,
  (d) hydroxy,
  (e) $C_{1-10}$ alkoxy,
  (f) $C_{1-5}$ alkoxycarbonyl,
  (g) $C_{1-5}$ acyloxy,
  (h) phenyl,
  (i) substituted phenyl in which the substituents ar X and Y;
(5) phenylamino;
(6) substituted phenylamino in which the substituents are X and Y;
(7) phenyl $C_{1-10}$ alkylamino; and
(8) substituted phenyl $C_{1-10}$ alkylamino in which the substituents are X and Y.

4. A compound of claim 3 wherein:
$R_1$ is selected from:
(1) $C_{1-10}$ alkyl;
(2) $C_{3-8}$ cycloalkyl;
(3) phenylamino; and
(4) substituted phenylamino in which the substituents are X and Y.

5. A compound of claim 4 wherein:
$R_2$ and $R_3$ are independently selected from:
(1) hydrogen;
(2) $C_{1-5}$ alkyl;
(3) $C_{1-5}$ alkyl substituted with hydroxy;
(4) $CH_2R_{12}$ in which $R_{12}$ is selected from:
  (a) $C_{1-5}$ alkoxy,
  (b) $C_{1-5}$ alkoxycarbonyl,
  (c) $C_{1-5}$ alkylacyloxy,
  (d) phenylacyloxy,
  (e) phenoxycarbonyl,
  (f) phenyl$C_{1-5}$ alkylacyloxy.
  (g) phenyl$C_{1-5}$ alkoxy,
  (h) phenyl $S(O)_n$,
  (i) substituted phenyl $S(O)_n$ in which the substituents are X and Y,
  (j) phenyl$C_{1-5}$ alkyl $S(O)_n$,
  (k) $C_{1-5}$ alkyl $S(O)_n$,
  (l) phenylaminoacyloxy,
  (m) $C_{1-5}$ alkylaminoacyloxy,
  (n) phenyl,
  (o) substituted phenyl in which the substituents are X and Y;
  (p) $C_{1-5}$ alkylacylamino;
  (q) phenyl$C_{1-5}$ alkylacylamino.

6. A compound of claim 5 wherein:
$R_2$ and $R_3$ are independently selected from:
(1) hydrogen;
(2) $C_{1-5}$ alkyl;
(3) $C_{1-5}$ substituted with hydroxy;
(4) $CH_2R_{12}$ in which $R_{12}$ is selected from:
  (a) $C_{1-5}$ alkoxy,
  (b) phenyl $S(O)_n$,
  (c) phenyl$C_{1-5}$ alkyl $S(O)_n$,
  (d) phenylaminoacyloxy,
  (e) $C_{1-5}$ alkylacylamino,
  (f) phenyl$C_{1-5}$ alkylacylamino.

7. A compound of claim 6 wherein:
$R_2$ and $R_3$ are independently selected from:
(1) hydrogen;
(2) $C_{1-5}$ alkyl;
(3) $C_{1-5}$ alkyl substituted with hydroxy;
(4) phenyl $S(O)_nCH_2$.

8. A compound of claim 7 wherein:
A is O; a is a single bond; and
$R_1$ is 2-methyl-2-butyl or 2-butyl; and
$R_2$ and $R_3$ are independently selected from $CH_3$, H, phenylthiomethyl and hydroxymethyl.

9. A compound of claim 8 selected from:
(1) 6(R)-[2-[8(S)-(2,2-dimethylbutyryloxy)-2(S)-methyl-5-oxa-6,6-dimethyl-1,2,3,4,4a(R),7,8,8a(R)-octahydronaphthyl-1(S)]ethyl]-4(R)-hydroxy-3,4,5,6-tetrahydro-2H-pyran-2-one;
(2) 6(R)-[2-[8(S)-(2,2-dimethylbutyryloxy)-2(S)-methyl-5-oxa-6(S)-(phenylthiomethyl, methyl)-1,2,3,4,4a(R),7,8,8a(R)-octahydronaphthyl-1(S)]ethyl]-4(R)-hydroxy-3,4,5,6-tetrahydro-2H-pyran-2-one;
(3) 6(R)-[2-[8(S)-(2,2-dimethylbutyrloxy)-2(S)-methyl-5-oxa-6(R)-(phenylthiomethyl, methyl)-1,2,3,4,4a(R),7,8,8a(R)-octahydronaphthyl-1(S)]ethyl]-4(R) hydroxy-3,4,5,6-tetrahydro-2H-pyran-2-one;
(4) 6(R)-[2-[8(S)-(2-methylbutyryloxy)-2(S)-methyl-5-oxa-6,6-dimethyl-1,2,3,4,4a(R),7,8,8a(R)-octahydronaphthyl-1(S)]ethyl]-4(R)-hydroxy-3,4,5,6-tetrahydro-2H-pyran-2-one;
(5) 6(R)-[2 [8(S)-(2,2-dimethylbutyryloxy)-2(S)-methyl-5- oxa-6(S)-(hydroxymethyl, methyl)-1,2,4,4a(R),7,8,8a(R)-octahydronaphthyl-1(S)]-ethyl]-4(R)-hydroxy-3,4,5,6-tetrahydro-2H-pyran-2-one;
(6) 6(R)-[2-[8(S)-(2,2-dimethylbutyryloxy) 2(S)-methyl-5-oxa-6(R)-(hydroxymethyl, methyl)-1,2,3,4,4a(R),7,8,8a(R)-octahydronaphthyl-1(S)]ethyl]-4-(R)-hydroxy-3,4,5,6-tetrahydro-2H-pyran-2-one;
(7) 6(R)- [2-[8(S)-(2,2-dimethylbutyryloxy)-2(S)-methyl-5 oxa-6(S)-(phenylthiomethyl, hydroxy methyl)-1,2,-3,4,4a(R),7,8,8a(R)-octahydronapht-hyl-1(S)]ethyl]4(R)-hydroxy-3,4,5,6-tetrahydro-2H-pryan-2-one;
(8) 6(R)-[2-[8(S)-(2,2-dimethylbutyryloxy)-2(S)-methyl-5-oxa-6(R)-(phenylthiomethyl, hydroxymethyl)-1,2,-3,4,4a(R),7,8,8a(R)-octahydronaphthyl-1(S)]ethyl]-4(R)-hydroxy-3,4,5,6-tetrahydro-2H-pyran-2-one;

and the corresponding ring opened dihydroxy acids and esters thereof.

10. A compound of claim 9 which is:
(1) 6(R)-[2-[8(S)-(2,2-dimethylbutyryloxy)-2(S)-methyl-5-oxa-6,6-dimethyl-1,2,3,4,4a(R),7,8,8a(R)-octahydronaphthyl-1(S)]ethyl]-4(R)-hydroxy 3,4,5,6-tetrahydro-2H-pyran-2-one;

and the corresponding ring opened dihydroxy acids and esters thereof.

11. A compound of claim 7 wherein:

A is S(O)$_n$; a is a single bond; and
R$_1$ is 2-methyl-2-butyl or 2-butyl; and
R$_2$ and R$_3$ are independently selected from CH$_3$, H and hydroxymethyl.

12. A compound of claim 1 wherein:
A is N—R$_{13}$; and
R$_1$ is selected from:
(1) C$_{1-10}$ alkyl;
(2) substituted C$_{1-10}$ alkyl in which one or more substituents(s) is selected from
  (a) halogen,
  (b) hydroxy,
  (c) C$_{1-10}$ alkoxy,
  (d) C$_{1-5}$ alkoxycarbonyl,
  (e) C$_{1-5}$ acyloxy,
  (f) C$_{3-8}$ cycloalkyl,
  (g) phenyl,
  (h) substituted phenyl in which the substituents are X and Y, and
  (i) oxo;
(3) C$_{3-8}$ cycloalkyl;
(4) substituted C$_{3-8}$ cycloalkyl in which one substituent is selected from
  (a) C$_{1-10}$ alkyl,
  (b) substituted C$_{1-10}$ alkyl in which the substituent is selected from
    (i) halogen,
    (ii) hydroxy,
    (iii) C$_{1-10}$ alkoxy
    (iv) C$_{1-5}$ acyloxy,
    (v) C$_{1-5}$ alkoxycarbonyl,
    (vi) phenyl,
    (vii) substituted phenyl in which the substituents are X and Y, and
    (viii) oxo,
  (c) halogen,
  (d) hydroxy,
  (e) C$_{1-10}$ alkoxy,
  (f) C$_{1-5}$ alkoxycarbonyl,
  (g) C$_{1-5}$ acyloxy,
  (h) phenyl,
  (i) substituted phenyl in which the substituents are X and Y;
(5) phenylamino;
(6) substituted phenylamino in which the substituents are X and Y;
(7) phenylC$_{1-10}$alkylamino; and
(8) substituted phenyl C$_{1-10}$ alkylamino in which the substituents are X and Y;
R$_2$ and R$_3$ are independently selected from
(1) hydrogen;
(2) C$_{1-10}$ alkyl;
(3) substituted C$_{1-10}$ alkyl in which one or more substituents is selected from:
  (a) halogen,
  (b) hydroxy,
  (c) amino;
(4) CH$_2$R$_{12}$ in which R$_{12}$ is selected from:
  (a) C$_{1-5}$ alkoxy,
  (b) C$_{1-5}$ alkoxycarbonyl,
  (c) C$_{1-5}$ alkylacyloxy,
  (d) phenylacyloxy,
  (e) phenoxycarbonyl,
  (f) phenylC$_{1-5}$alkylacyloxy,
  (g) phenylC$_{1-5}$alkoxy,
  (h) C$_{1-5}$ alkylamino,
  (i) di(C$_{1-5}$alkylamino),
  (j) phenylamino,
  (k) substituted phenylamino in which the substituents are X and Y,
  (l) phenyl C$_{1-5}$ alkylamino,
  (m) substituted phenyl C$_{1-5}$ alkyl amino in which the substituents are X and Y,
  (n) C$_{3-8}$ cycloalkyl,
  (o) phenyl,
  (p) substituted phenyl in which the substituents are X and Y,
  (q) phenylS(O)$_n$,
  (r) substituted phenylS(O)$_n$ in which the substituents are X and Y,
  (s) phenyl C$_{1-5}$ alkylS(O)$_n$,
  (t) C$_{1-5}$ alkylS(O)$_n$,
  (u) phenylaminoacyloxy,
  (v) C$_{1-5}$ alkylaminoacyloxy,
  (w) C$_{1-5}$ alkylacylamino,
(5) R$_2$ and R$_3$ together with the carbon atom to which they are attached form a C$_{3-8}$ carbocyclic ring.

13. A compound of claim 12 wherein:
R$_1$ is selected from:
(1) C$_{1-10}$alkyl;
(2) C$_{3-8}$ cylcoalkyl;
(3) phenylamino; and
(4) substituted phenylamino in which the substituents are X and Y;
R$_{13}$ is selected from:
(1) hydrogen;
(2) C$_{1-5}$ alkyl;
(3) phenylC$_{1-5}$ alkyl;
(4) C$_{1-5}$ alkylcarbonyl.

14. A compound of claim 13 wherein
R$_2$ and R$_3$ are independently selected from:
(1) hydrogen;
(2) C$_{1-5}$alkyl;
(3) C$_{1-5}$alkyl substituted with hydroxy;
(4) CH$_2$R$_{12}$ in which R$_{12}$ is selected from:
  (a) C$_{1-5}$alkoxy,
  (b) C$_{1-5}$alkoxycarbonyl,
  (c) C$_{1-5}$alkylacyloxy,
  (d) phenylacyloxy,
  (e) phenoxycarbonyl,
  (f) phenylC$_{1-5}$alkylacyloxy,
  (g) phenylC$_{1-5}$alkoxy,
  (h) phenyl S(O)$_n$,
  (i) substituted phenyl S(O)$_n$ in which the substituents are X and Y,
  (j) phenylalkyl S(O)$_n$,
  (k) C$_{1-5}$alkyl S(O)$_n$,
  (l) phenylaminoacyloxy,
  (m) C$_{1-5}$alkylaminoacyloxy,
  (n) phenyl,
  (o) substituted phenyl in which the substituents are X and Y.

15. A hypocholesterolemic, hypolipidemic pharmaceutical composition comprising a pharmaceutically acceptable carrier and a therapeutically effective amount of a compound as defined in claim 1.

16. A composition of claim 15 in which the compound is selected from:
(1) 6(R)-[2-[8(S)-(2,2-dimethylbutyryloxy)-2(S)-methyl-5-oxa-6,6-dimethyl-1,2,3,4,4a(R),7,8,8a(R)-octahydronaphthyl-1(S)]ethyl]-4(R)-hydroxy-3,4,5,6 -tetrahydro-2H-pyran-2-one;
(2) 6(R)-[2-[8(S)-(2,2-dimethylbutyryloxy)-2(S)-methyl-5-oxa-6(S)-(phenylthiomethyl, methyl)-

1,2,3,4,4a(R),7,8,8a(R) octahydronaphthyl-1(S)]ethyl]-4(R)-hydroxy-3,4,5,6-tetrahydro-2H-pyran-2-one;

(3) 6(R)-[2-[8(S)-(2,2-dimethylbutyryloxy)-2(S)-methyl-5-oxa-6(R)-(phenylthiomethyl, methyl)-1,2,3,4,4a(R),7,8,8a(R)-octahydronaphthyl-1(S)]ethyl]-4(R)-hydroxy-3,4,5,6-tetrahydro-2H-pyran-2-one;

(4) 6(R)-[2-[8(S)-(2-methylbutyryloxy)-2(S)-methyl-5-oxa-6,6-dimethyl-1,2,3,4,4a(R),7,8,8a(R)-octahydronaphthyl-1(S)]ethyl]-4(R)-hydroxy-3,4,5,6-tetrahydro-2H-pyran-2-one;

(5) 6(R)-[2-[8(S)-(2,2-dimethylbutyryloxy)-2(S)-methyl-5-oxa-6(S)-(hydroxymethyl, methyl)-1,2,3,4,4a(R),7,8,8a(R)-octahydronaphthyl-1(S)]ethyl]-4(R)-hydroxy-3,4,5,6-tetrahydro-2H-pyran-2-one;

(6) 6(R)-[2-[8(S)-(2,2-dimethylbutyryloxy)-2(S)-methyl-5-oxa-6(R)-(hydroxymethyl, methyl)-1,2,3,4,4a(R),7,8,8a(R)-octahydronaphthyl-1(S)]ethyl]-4-(R)-hydroxy-3,4,5,6-tetrahydro-2H-pyran-2-one;

(7) 6(R)-[2-[8(S)-(2,2-dimethylbutyryloxy)-2(S)-methyl-5-oxa-6(S)-(phenylthiomethyl, hydroxymethyl)-1,2,-3,4,4a(R),7,8,8a(R)-octahydronaphthyl-1(S)]ethyl]-4(R)-hydroxy-3,4,5,6-tetrahydro-2H-pyran-2-one;

(8) 6(R)-[2-[8(S)-(2,2-dimethylbutyryloxy)-2(S)-methyl-5-oxa-6(R)-(phenylthiomethyl, hydroxymethyl)-1,2,-3,4,4a(R),7,8,8a(R)-octahydronaphthyl-1(S)]ethyl]-4(R)-hydroxy-3,4,5,6-tetrahydro-2H-pyran-2-one; and the corresponding ring opened dihydroxy acids and esters thereof.

17. A method of inhibiting cholesterol biosynthesis comprising the administration to a subject in need of such treatment a nontoxic therapeutically effective amount of a compound of claim 1.

18. A method of claim 17 in which the compound is selected from:

(1) 6(R)-[2-[8(S)-(2,2-dimethylbutyryloxy)-2(S)-methyl-5-oxa-6,6-dimethyl-1,2,3,4,4a(R),7,8,8a(R)-octahydronaphthyl-1(S)]ethyl]-4(R)-hydroxy-3,4,5,6-tetrahydro-2H-pyran-2-one;

(2) 6(R)-[2-[8(S)-(2,2-dimethylbutyryloxy)-2(S)-methyl-5-oxa-6(S)-(phenylthiomethyl, methyl)-1,2,3,4,4a(R),7,8,8a(R)-octahydronaphthyl-1(S)]-ethyl]-4(R)-hydroxy-3,4,5,6-tetrahydro-2H-pyran-2-one;

(3) 6(R)-[2-[8(S)-(2,2-dimethylbutyryloxy)-2(S)-methyl-5-oxa-6(R)-(phenylthiomethyl, methyl)-1,2,3,4,4a(R),7,8,8a(R)-octahydronaphthyl-1(S)]-ethyl]-4(R)-hydroxy-3,4,5,6-tetrahydro-2H-pyran-2-one;

(4) 6(R)-[2-[8(S)-(2-methylbutyryloxy)-2(S)-methyl-5-oxa-6,6-dimethyl-1,2,3,4,4a(R),7,8,8a(R)-octahydronaphthyl-1(S)]ethyl]-4(R)-hydroxy-3,4,5,6-tetrahydro-2H-pyran-2-one;

(5) 6(R)-[2-[8(S)-(2,2-dimethylbutyryloxy)-2(S)-methyl-5-oxa-6(S)-(hydroxymethyl, methyl)-1,2,3,4,4a(R),7,8,8a(R)-octahydronaphthyl-1(S)]ethyl]-4(R)-hydroxy-3,4,5,6-tetrahydro-2H-pyran-2-one;

(6) 6(R)-[2-[8(S)-(2,2-dimethylbutyryloxy)-2(S)-methyl-5-oxa-6(R)-(hydroxymethyl, methyl)-1,2,3,4,4a(R),7,8,8a(R)-octahydronaphthyl-1(S)] ethyl]-4(R)-hydroxy-3,4,5,6-tetrahydro-2H-pyran-2-one;

(7) 6(R)-[2-[8(S)-(2,2-dimethylbutyryloxy)-2(S)-methyl-5-oxa-6(S)-(phenylthiomethyl, hydroxymethyl)-1,2,-3,4,4a(R),7,8,8a(R)-octahydronaphthyl-1(S)]ethyl]-4(R)-hydroxy-3,4,5,6-tetrahydro-2H-pyran-2-one;

(8) 6(R)-[2-[8(S)-(2,2-dimethylbutyryloxy)-2(S)-methyl-5-oxa-6(R)-(phenylthiomethyl, hydroxymethyl)-1,2,-3,4,4a(R),7,8,8a(R)-octahydronaphthyl-1(S)]ethyl]-4(R)-hydroxy-3,4,5,6-tetrahydro-2H-pyran-2-one; and the corresponding ring opened dihydroxy acids and esters thereof.

* * * * *